(12) United States Patent
Rava et al.

(10) Patent No.: US 11,286,520 B2
(45) Date of Patent: *Mar. 29, 2022

(54) METHOD FOR DETERMINING COPY NUMBER VARIATIONS

(71) Applicant: Verinata Health, Inc., Redwood City, CA (US)

(72) Inventors: Richard P Rava, Redwood City, CA (US); Brian Kent Rhees, Chandler, AZ (US)

(73) Assignee: Verinata Health, Inc., Redwood City, CA (US)

( * ) Notice: Subject to any disclaimer, the term of this patent is extended or adjusted under 35 U.S.C. 154(b) by 1163 days.

This patent is subject to a terminal disclaimer.

(21) Appl. No.: 15/664,043

(22) Filed: Jul. 31, 2017

(65) Prior Publication Data
US 2017/0327884 A1 Nov. 16, 2017

Related U.S. Application Data

(63) Continuation of application No. 13/333,832, filed on Dec. 21, 2011, now abandoned, which is a
(Continued)

(51) Int. Cl.
*C12Q 1/6869* (2018.01)
*C12Q 1/6809* (2018.01)
(Continued)

(52) U.S. Cl.
CPC ......... *C12Q 1/6869* (2013.01); *C12Q 1/6806* (2013.01); *C12Q 1/6809* (2013.01);
(Continued)

(58) Field of Classification Search
None
See application file for complete search history.

(56) References Cited

U.S. PATENT DOCUMENTS 5,888,740 A 3/1999 Han
5,994,057 A 11/1999 Mansfield
(Continued)

FOREIGN PATENT DOCUMENTS

CA 2825984 A1 9/2011
CN 100519761 7/2009
(Continued)

OTHER PUBLICATIONS

U.S. Appl. No. 13/009,718, filed Jan. 19, 2010, Rava.
(Continued)

*Primary Examiner* — Olivia M. Wise
(74) *Attorney, Agent, or Firm* — Mueting Raasch Group

(57) ABSTRACT

A method for determining copy number variations (CNV) of a sequence of interest in a test sample that comprises a mixture of nucleic acids that are known or are suspected to differ in the amount of one or more sequence of interest. The method comprises a statistical approach that accounts for accrued variability stemming from process-related, inter-chromosomal and inter-sequencing variability. The method is applicable to determining CNV of any fetal aneuploidy, and CNVs known or suspected to be associated with a variety of medical conditions.

21 Claims, 20 Drawing Sheets

Related U.S. Application Data continuation of application No. 12/958,352, filed on Dec. 1, 2010, now abandoned.

(60) Provisional application No. 61/407,017, filed on Oct. 26, 2010, provisional application No. 61/455,849, filed on Oct. 26, 2010, provisional application No. 61/360,837, filed on Jul. 1, 2010, provisional application No. 61/296,358, filed on Jan. 19, 2010.

(51) Int. Cl.

| | |
|---|---|
| *G16B 30/10* | (2019.01) |
| *G16B 20/10* | (2019.01) |
| *C12Q 1/6883* | (2018.01) |
| *C12Q 1/6806* | (2018.01) |

(52) U.S. Cl.
CPC ............. *G16B 20/10* (2019.02); *G16B 30/10* (2019.02); *C12Q 1/6883* (2013.01); *C12Q 2600/106* (2013.01); *C12Q 2600/112* (2013.01)

(56) References Cited

U.S. PATENT DOCUMENTS

| | | |
|---|---|---|
| 6,258,540 B1 | 7/2001 | Lo et al. |
| 6,403,315 B1 | 6/2002 | Drmanac |
| 6,440,706 B1 | 8/2002 | Vogelstein et al. |
| 6,555,315 B1 | 4/2003 | Short |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 8,551,707 B2 | 10/2013 | Oeth et al. |
| 9,260,745 B2 | 2/2016 | Rava et al. |
| 9,657,342 B2* | 5/2017 | Rava .................. C12Q 1/6809 |
| 10,941,442 B2* | 3/2021 | Rava ..................... G16B 30/10 |
| 2002/0142324 A1 | 10/2002 | Wang et al. |
| 2003/0044388 A1 | 3/2003 | Lo et al. |
| 2003/0064368 A1 | 4/2003 | Sakai et al. |
| 2003/0194704 A1 | 10/2003 | Penn et al. |
| 2004/0209299 A1 | 10/2004 | Pinter et al. |
| 2005/0221341 A1 | 10/2005 | Shimkets et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0178835 A1 | 8/2006 | Marks |
| 2006/0257895 A1 | 11/2006 | Pinkel et al. |
| 2006/0286558 A1 | 12/2006 | Novoradovskaya et al. |
| 2007/0087345 A1 | 4/2007 | Olson-Munoz et al. |
| 2007/0134658 A1 | 6/2007 | Bohmer et al. |
| 2007/0202525 A1 | 8/2007 | Quake et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker et al. |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0170114 A1 | 7/2009 | Quake et al. |
| 2009/0215042 A1 | 8/2009 | Sella-Tavor et al. |
| 2009/0270601 A1 | 10/2009 | Benner et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0196426 A1 | 8/2010 | Skog et al. |
| 2010/0216151 A1 | 8/2010 | Lapidus et al. |
| 2010/0216153 A1 | 8/2010 | Lapidus et al. |
| 2010/0285537 A1 | 11/2010 | Zimmerman |
| 2011/0003293 A1 | 1/2011 | Stoughton et al. |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1 | 12/2011 | Fan et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0165203 A1 | 6/2012 | Quake et al. |
| 2012/0183963 A1 | 7/2012 | Stoughton et al. |
| 2012/0184449 A1 | 7/2012 | Hixson et al. |
| 2012/0208710 A1 | 8/2012 | Fan et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2012/0264121 A1 | 10/2012 | Rava et al. |
| 2012/0270739 A1 | 10/2012 | Rava et al. |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |
| 2016/0194703 A1 | 7/2016 | Rava et al. |
| 2016/0232290 A1 | 8/2016 | Rava et al. |

FOREIGN PATENT DOCUMENTS

| | | |
|---|---|---|
| CN | 102127818 A | 7/2011 |
| CN | 102212614 A | 10/2011 |
| CN | 102409043 A | 4/2012 |
| EP | 2334812 | 6/2011 |
| EP | 2513339 | 10/2012 |
| GB | 2479471 | 10/2011 |
| GB | 2479476 | 10/2011 |
| GB | 2479080 | 1/2012 |
| GB | 2484764 | 4/2012 |
| GB | 2485635 | 11/2012 |
| GB | 2485644 | 11/2012 |
| GB | 2485645 | 11/2012 |
| JP | 2006-508632 | 3/2006 |
| JP | 2010-534069 | 11/2010 |
| WO | 1996/19586 | 6/1996 |
| WO | 1998/44151 | 10/1998 |
| WO | 00/18957 | 4/2000 |
| WO | WO 01/90415 A2 | 11/2001 |
| WO | WO 02/02772 A2 | 1/2002 |
| WO | 2003/004677 | 1/2003 |
| WO | 03/074740 | 9/2003 |
| WO | 2003/074723 | 9/2003 |
| WO | 2004/078999 | 9/2004 |
| WO | WO 2005/003375 A2 | 1/2005 |
| WO | 2006/010610 | 2/2006 |
| WO | 2006/028152 | 3/2006 |

(56) References Cited

FOREIGN PATENT DOCUMENTS

| WO | 2006/028153 | 3/2006 |
|---|---|---|
| WO | 2007/092473 | 8/2007 |
| WO | 2007/100911 | 9/2007 |
| WO | 2007/147074 | 12/2007 |
| WO | 2007/147079 | 12/2007 |
| WO | 2009/013492 | 1/2009 |
| WO | 2009/013496 | 1/2009 |
| WO | 2009/046445 | 4/2009 |
| WO | 2010/033578 | 3/2010 |
| WO | 2011/051283 | 5/2011 |
| WO | 2011/057094 | 5/2011 |
| WO | 2011/090556 | 7/2011 |
| WO | 2011/090557 | 7/2011 |
| WO | 2011/090558 | 7/2011 |
| WO | 2011/090559 | 7/2011 |
| WO | 2011/091046 | 7/2011 |
| WO | 2011/091063 | 7/2011 |
| WO | 2012/019187 | 2/2012 |
| WO | 2012/019193 | 2/2012 |
| WO | 2012/019198 | 2/2012 |
| WO | 2012/019200 | 2/2012 |
| WO | 2012/071621 | 6/2012 |
| WO | 2012/078792 | 6/2012 |
| WO | 2012/088348 | 6/2012 |
| WO | 2012/103031 | 8/2012 |
| WO | 2012/108920 | 8/2012 |
| WO | 2012/142334 | 10/2012 |
| WO | 2013/015793 | 1/2013 |
| WO | 2014/014498 | 1/2014 |

OTHER PUBLICATIONS

U.S. Appl. No. 13/012,222, filed Jan. 24, 2010, Chuu et al.
U.S. Appl. No. 61/371,605, filed Aug. 6, 2010, Oliphant et al.
U.S. Appl. No. 12/958,347, filed Dec. 1, 2010, Rava et al.
U.S. Appl. No. 12/958,352, filed Dec. 1, 2010, Rava et al.
U.S. Appl. No. 12/958,353, filed Dec. 1, 2010, Rava et al.
U.S. Appl. No. 12/958,356, filed Dec. 1, 2010, Quake et al.
U.S. Appl. No. 13/087,842, filed Apr. 15, 2011, Rava.
U.S. Appl. No. 13/191,366, filed Jul. 26, 2011, Rava et al.
U.S. Appl. No. 13/333,832, filed Dec. 21, 2011, Rava et al.
U.S. Appl. No. 13/364,809, filed Feb. 2, 2012, Rava et al.
U.S. Appl. No. 13/365,134, filed Feb. 2, 2012, Rava et al.
U.S. Appl. No. 13/365,240, filed Feb. 2, 2012, Quake et al.
U.S. Appl. No. 13/400,028, filed Feb. 17, 2012, Rava et al.
U.S. Appl. No. 13/433,232, filed Mar. 28, 2012, Stoughton et al.
U.S. Appl. No. 13/452,083, filed Apr. 20, 2012, Fan et al.
U.S. Appl. No. 13/461,582, filed May 1, 2012, Rava et al.
"Combined Search and Examination Report in GB Patent Application No. 1118396.9", dated Mar. 16, 2012.
"Combined Search and Examination Report in GB Patent Application No. 1118398.5", dated Mar. 16, 2012.
"European Search Report in EP Patent Application No. 10825822.9", dated Feb. 22, 2012, 4 pages.
"European Search Report in EP Patent Application No. 10830938.6", dated Feb. 22, 2012, 4 pages.
"European Search Report in EP Patent Application No. 10830939.4", dated Feb. 22, 2012, 4 pages.
"Examination Report in EP Patent Application No. 10825822.9", dated Oct. 17, 2012.
"Examination Report in EP Patent Application No. 10825822.9", dated Apr. 10, 2013.
"Examination Report in EP Patent Application No. 10825822.9", dated Mar. 19, 2012, 5.
"Examination Report in EP Patent Application No. 10830938.6", dated Oct. 18, 2012.
"Examination Report in EP Patent Application No. 10830938.6", dated Mar. 16, 2012.
"Examination Report in EP Patent Application No. 10830938.6", dated Apr. 10, 2013.
"Examination Report in EP Patent Application No. 10830939.4", dated Oct. 17, 2012.
"Examination Report in EP Patent Application No. 10830939.4", dated Mar. 16, 2012.
"Examination Report in EP Patent Application No. 10830939.4", dated Apr. 10, 2013.
"Examination Report in EP Patent Application No. 11744148.5", dated Nov. 20, 2012.
"Examination Report in EP Patent Application No. 11744148.5", dated Apr. 10, 2013.
"Examination Report in GB Patent Application No. 1106394.8", dated Jun. 24, 2011.
"Examination Report in GB Patent Application No. 1107268.3", dated Nov. 15, 2011.
"Examination Report in GB Patent Application No. 1107268.3", dated Dec. 7, 2011.
"Examination Report in GB Patent Application No. 1107268.3", dated Jul. 15, 2011.
"Examination Report in GB Patent Application No. 1108794.7", dated Jul. 15, 2011.
"Examination Report in GB Patent Application No. 1108795.4", dated Dec. 16, 2011.
"Examination Report in GB Patent Application No. 1108795.4", dated Mar. 9, 2012.
"Examination Report in GB Patent Application No. 1108795.4", dated Jul. 15, 2011.
"Examination Report in GB Patent Application No. 1114713.9", dated Dec. 7, 2011.
"Examination Report in GB Patent Application No. 1114713.9", dated Mar. 6, 2012.
"Examination Report in GB Patent Application No. 1118396.9", dated Aug. 14, 2012.
"Examination Report in GB Patent Application No. 1118398.5", dated Aug. 17, 2012.
"Extended European Search Report in EP Patent Application No. 11175845.4", dated Nov. 17, 2011.
"Extended European Search Report in EP Patent Application No. 11735131.2", dated Jun. 3, 2013.
"Extended European Search Report in EP Patent Application No. 14192156.9", dated Apr. 7, 2015.
"Final Office Action in U.S. Appl. No. 12/958,353", dated Sep. 10, 2013.
"Final Office Action in U.S. Appl. No. 12/958,356", dated Aug. 22, 2013.
"Final Office Action in U.S. Appl. No. 13/364,809", dated Feb. 19, 2013.
"Final Office Action in U.S. Appl. No. 13/365,134", dated Feb. 20, 2013.
"International Preliminary Report on Patentability issued in International Patent Application No. PCT/US2013/023909", dated Jan. 20, 2015.
"International Search Report in PCT Application No. PCT/US2010/058606", dated Feb. 28, 2011.
"International Search Report in PCT Application No. PCT/US2010/058609", dated Apr. 4, 2011.
"International Search Report in PCT Application No. PCT/US2010/058612", dated May 19, 2011.
"International Search Report in PCT Application No. PCT/US2010/058614", dated Mar. 1, 2011.
"International Search Report in PCT Application No. PCT/US2011/021729", dated Apr. 11, 2011.
"International Search Report in PCT Application No. PCT/US2011/045412", dated Feb. 24, 2012.
"International Search Report in PCT Application No. PCT/US2013/023909", dated Dec. 12, 2013.
"International Search Report in PCT Application No. PCT/US2013/051399", dated Oct. 7, 2013.
"Notice of Allowance in U.S. Appl. No. 12/696,509", dated Mar. 1, 2012.
"Notice of Allowance in U.S. Appl. No. 13/452,083", dated Jul. 12, 2012.
"Notice of Allowance in U.S. Appl. No. 13/555,010", dated Jun. 3, 2015.

(56) References Cited

OTHER PUBLICATIONS

"Notice of Allowance in U.S. Appl. No. 13/555,037", dated Jun. 16, 2015.
"Office Action in U.S. Appl. No. 13/191,366", dated Aug. 2, 2013.
"Office Action in U.S. Appl. No. 12/393,833", dated Jun. 5, 2012.
"Office Action in U.S. Appl. No. 12/958,352", dated Oct. 10, 2012.
"Office Action in U.S. Appl. No. 12/958,352", dated Aug. 1, 2013.
"Office Action in U.S. Appl. No. 12/958,353", dated Dec. 20, 2012.
"Office Action in U.S. Appl. No. 12/958,356", dated Jan. 11, 2013.
"Office Action in U.S. Appl. No. 13/333,832", dated May 23, 2012.
"Office Action in U.S. Appl. No. 13/364,809", dated Aug. 10, 2012.
"Office Action in U.S. Appl. No. 13/365,134", dated Aug. 15, 2012.
"Office Action in U.S. Appl. No. 13/368,035", dated Mar. 13, 2012.
"Office Action in U.S. Appl. No. 13/482,964", dated Feb. 4, 2014.
"Office Action in U.S. Appl. No. 13/555,010", dated Oct. 27, 2014.
"Office Action in U.S. Appl. No. 13/555,010", dated May 22, 2014.
"Office Action in U.S. Appl. No. 13/555,037", dated Nov. 13, 2014.
"Office Action in U.S. Appl. No. 13/600,043", dated Jun. 10, 2015.
"Office Action issued in Australian Patent Application No. 2011207561 (ARTEP001AU)", dated Aug. 29, 2013.
"PCT International Search Report mailed in PCT application No. PCT/US2012/033391", dated Mar. 11, 2013.
"Search Report and Written Opinion in Singapore Application No. 201400043-4", dated Apr. 1, 2015.
"Search Report in GB Patent Application No. 1114713.9", dated Dec. 6, 2011.
"Search Report relating to claims 16-23, in part 24-31 in GB Patent Application No. 1114713.9", dated Apr. 17, 2012.
"Search Report relating to claims 8-11, in part 12-15 in GB Patent Application No. 1114713.9", dated Apr. 17, 2012.
Angeloni, D., "Molecular analysis of deletions in human chromosome 3p21 and the role of resident cancer genes in disease", Briefings Functional Genomics, vol. 6(1), May 24, 2007, 19-39.
Ashoor et al., "Chromosome-selective sequencing of maternal plasma cell-free DNA for first-trimester detection of trisomy 21 and trisomy 18", Am J Obstet Gynecol, 206(4), Apr. 2012, 322.e1-5.
Ashoor et al., "Fetal Fraction in maternal plasma cell-free DNA at 11-13 weeks' gestation: effect of maternal and fetal factors", Fetal Diagn Ther, published online, May 4, 2012, 7 pages.
Bentley et al., "Accurate whole human genome sequencing using reversible terminator chemistry", Nature, vol. 456, Nov. 6, 2008, 53-59.
Beroukhim et al., "The landscape of somatic copy-number alteration across human cancers", Nature, vol. 463, Feb. 2010, 899-905.
Borsting, "Multiplex PCR, amplicon size and hybridization efficiency on the NanoChip electronic microarray", Int J. Legal Med. vol. 118, 2004, 75-82.
Botezatu et al., "Genetic Analysis of DNA excreted in urine: a new approach for detecting specific genomic DNA sequences from cells dying in an organism", Clin Chem. 46(8 Pt1), Aug. 2000, 1078-84.
Bowcock et al., "Exclusion of the Retinablastoma Gene and Chromosome 13q as the Site of a Primary Lesion for Human Breast Cancer", Am J Hum Genet, vol. 46, 1990, 12.
Brosens et al., "Deletion of chromosome 4q predicts outcome in stage II colon cancer patients", Analytical Cellular Pathology / Cellular Oncology 33, 2010, 95-104.
Buck et al., "Design Strategies and Performance of Custom DNA Sequencing Primers", Biotechniques vol. 27, 1999, 528-536.
Butler et al., "Short tandem repeat typing technologies used in human identity testing", Biotechniques 43(4), Oct. 2007, ii-v.
Butler et al., "The Development of reduced size STR amplicons as tools for analysis of degraded DNA", J. Forensic Sci 48(5), 2003, 1054-64.
Caramazza et al., "Chromosome 1 abnormalities in myeloid malignancies: a literature survey and karyotype-phenotype associations", European Journal of Haematology, vol. 84, 2010, 191-200.
Chan et al., "Size Distributions of maternal and fetal DNA in Maternal Plasma", Clin. Chem 50(1), Jan. 2004, 88-92.
Chen et al., "Detection in Fecal DNA of Colon Cancer-Specific hylation of the Nonexpressed Vimentin Gene", Journal of the National Cancer Institute, vol. 97, No. 15,, Aug. 2, 2005, 1124-1132.
Chen et al., "Microsatellite alterations in plasma DNA of small cell lung cancer patients", Nat Med. 2(9), 1996, 1033-5.
Chiang et al., "High-resolution mapping of copy-number alterations with massively parallel sequencing", Nature Methods, vol. 6, No. 1 (2009), published online: doi:10.1038/nmeth.1276, Jan. 2009, 99-103.
Chiu et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu et al., "Non-invasive prenatal assessment of trisomy 21 by multiplexed maternal plasma DNA sequencing: large scale validity study", BMJ 342, Jan. 11, 2011, c7401.
Chiu et al., "Non-invasive prenatal diagnosis by single molecule counting technologies", Trends Genet. 25 (7), Jul. 1, 2009, 324-331 pp.
Chiu et al., "Noninvasive prenatal diagnosis empowered by high-throughput sequencing", Prenat Diagn. 32(4), Mar. 30, 2012, 401-406.
Chiu et al., "Noninvasive prenatal diagnosis of fetal chromosomal aneuploidy by massively parallel genomic sequencing of DNA in maternal plasma", PNAS, vol. 105, No. 51, Dec. 23, 2008, pp. 20458-20463.
Chu et al., "Statistical model for whole genome sequencing and its application to minimally invasive of fetal genetic disease", Bioinformatics 25(10), May 15, 2009, 1244-1250.
Clarke et al., "Effects of chemotherapy and hormonal therapy for early breast cancer on recurrence and 15-year survival: an overview of randomised trials", Lancet vol. 365, 2005, 1687-1717.
Clarke et al., "Effects of radiotherapy and of differences in the extent of surgery for early breast cancer on local recurrence and 15-year survival: an overview of the randomised trials", Lancet vol. 366, 2005, 2087-2106.
Coble et al., "Characterization of New MiniSTR Loci to Aid Analysis of Degraded DNA", J Forensic Sci, 50(1), Jan. 2005, 43-53.
Deng et al., "Enumeration and microfluidic chip separation of circulating fetal cells early in pregnancy from maternal blood", American Journal of Obstetrics & Gynecology, vol. 199, Issue 6, Dec. 2008, S134.
Dhallan et al., "A non-invasive test for prenatal diagnosis based on fetal DNA present in maternal blood: a preliminary study", Lancet 369(9560), Feb. 10, 2007, 474-481.
Ding et al., "MS analysis of single-nucleotide differences in circulating nucleic acids: Application to noninvasive prenatal diagnosis", Proceedings of National Academy of Sciences 101(29), 2004, pp. 10762-10767.
Dixon et al., "Analysis of artificially degraded DNA using STRs and SNPs—results of a collaborative European (EDNAP) exercise", Forensic Sci Int 164(1), Dec. 1, 2006, 33-44.
Ehrich "Noninvasive detection of fetal trisomy 21 by sequencing of DNA in maternal blood: a study in a clinical setting", Am J Obstet Gynecol, 204(3), Mar. 2011, 205.e1-11.
Eisenmann et al., "5q- myelodysplastic syndromes: chromosome 5q genes direct a tumor-suppression network sensing actin dynamics", Oncogene, vol. 28, 2009, 3429-3441.
Fan et al., "Analysis of the size distributions of fetal and maternal cell-free DNA by paired-end sequencing", Clin. Chem 56(8), Aug. 1, 2010, 1279-1286.
Fan et al., "Detection of aneuploidy with digital polymerase chain reaction", Anal Chem. 79(19), Oct. 1, 2007, 7576-7579.
Fan et al., "In principle method for noninvasive determination of the fetal genome", Nature Precedings: Nature Precedings 10.1038/npre, Dec. 8, 2010, 5373.1.
Fan et al., "Microfluidic digital PCR enables rapid prenatal diagnosis of fetal aneuploidy", Am J Obstet Gynecol 200(5), May 2009, 543.e1-7.
Fan et al., "Noninvasive diagnosis of fetal aneuploidy by shotgun sequencing DNA from maternal blood", Proceedings of the National Academy of Sciences, vol. 105, No. 42, also available at: http://www.pnas.org/cgi/doi/10.1073/pnas.0808319105, Oct. 21, 2008, 16266-71.

(56) References Cited

OTHER PUBLICATIONS

Fan et al., "Sensitivity of noninvasive prenatal detection of fetal aneuploidy from maternal plasma using shotgun sequencing is limited only by counting statistics", PLoS One 5(5), May 3, 2010, e10439.
Fan et al., "Supporting Information", 10.1073/pnas.0808319105, PNAS 105(42):16222, Oct. 2008, 7 pages.
Fan et al., "Whole-genome molecular haplotyping of single cells", Nature Biotechnology, Advanced Online Publication, Dec. 19, 2010, 9 pages.
Fonatsch, C., "The role of chromosome 21 in hematology and oncology", Genes, Chromosomes and Cancer, vol. 49, Issue 6, Jun. 2010, 497-508.
Frohling et al., "Chromosomal Abnormalities in Cancer", New England Journal of Medicine, vol. 359, 2008, 722-734.
Ghanta et al., "Non-Invasive Prenatal Detection of Trisomy 21 Using Tandem Single Nucleotide Polymorphisms", PLos ONE, vol. 5, Issue 10, e13184, Oct. 2010, 10 pages.
Goossens et al., "Simultaneous Mutation and Copy Number Variation (CNV) Detection by Multiplex PCR-Based GS-FLX Sequencing", Human Mutation, vol. 30, Issue 3, Dec. 2008, 472-476.
Grubweiser et al., "A new "miniSTR-multiplex" displaying reduced amplicon lengths for the analysis of degrade DNA", Int J. Legal Med 120(2), 2006, 115-20.
Hanson et al., "Whole genome amplification strategy for forensic genetic analysis using single or few cell equivalents of genomic DNA", Anal Biochem. 346(2), Nov. 15, 2005, 246-57.
Harris et al., "Single-Molecule DNA Sequencing of a Viral Genome", Science 320, Apr. 4, 2008, 106-109 and Suppl. Materials 1-25.
Harrison et al., "Polymer-stimulated ligation: enhanced ligation of oligo- and polynucleotides by T4 RNA ligase in polymer solutions", Nucleic Acids Research vol. 12 No. 21 1984, 1984, 8235-51.
Hayashi et al., "Regulation of inter- and intramolecular ligation with T4 DNA ligase in the presence of polyethylene glycol", Nucleic Acids Res. 14(19), Oct. 10, 1986, 7617-31.
Hill et al., "Characterization of 26 new miniSTR Loci", Poster #44—17th International Symposium on Human Identification, Nashville, TN, October 10-12, 2006, 1.
Hoffman et al., "The genome-enabled electronic medical record", Journal of Biomedical Informatics 10 (2007) published online, Mar. 15, 2006, 44-46.
Howe et al., "Retinoblastoma growth suppressor and a 300-kDa protein appear to regulate cellular DNA synthesis", Proc. Natl. Acad. Sci. USA, vol. 87, Aug. 1990, 5883-5887.
Huang, "Isolation of cell-free DNA from maternal plasma using manual and automated systems", Methods Mol Biol. 444, 2008, 203-8.
Hung "Detection of circulating fetal nucleic acids: a review of methods and applications", J Clin Pathol 62(4), 2009, 308-13.
Illanes et al., "Early detection of cell-free fetal DNA in maternal plasma", Early Human Dev., vol. 83, Issue 9, Sep. 2007, 563-566.
Illumina, "Preparing Samples for ChIP sequencing of DNA", E-pub at grcf.jhmi.edu/hts/protocols/11257047_ChIP_Sample_Prep.pdf., 2007, 15.
International, "The International HapMap Consortium Project", Nature 426:789-96, 2003.
Jama et al., "Quantification of cell-free fetal DNA Levels on maternal plasma by STR analysis", 2010 ACMG Annual Clinical Genetics Meeting, 2010, 2 pages.
Jensen et al., "Detection of Microdeletion 22q11.2 in a Fetus by Next-Generation Sequencing of Maternal Plasma", Clinical Chemistry 58:7; doi:10.1373/clinchem.2011.180794, May 4, 2012, 1148-1151.
Jongsma et al., "Molecular evidence for putative tumour suppressor genes on chromosome 13q specific to BRCA1 related ovarian and fallopian tube cancer", J Clin Pathol: Mol Pathol., vol. 55(5), 2002, 305-309.
Jorgez et al., "Improving Enrichment of circulating fetal DNA for genetic testing: size fractionation followed by whole gene amplification", Fetal Diagnosis and Therapy, Karger Basel, CH, vol. 25, No. 3, 2009, pp. 314-319.
Ju et al., "Four-Color DNA Sequencing by Synthesis Using Cleavable Florescent Nucleotide Reversible Terminators", PNAS vol. 103, No. 52, 2006, 19635-19640.
Kidd et al., "Developing a SNP panel for forensic identification of individuals", Forensic Science International 164 ( 2006), 2006, 20-32.
Kim et al., "rSW-seq: algorithm for detection of copy number alterations in deep sequencing data", BMC Bioinformatics, vol. 11, Aug. 18, 2010, 432.
Koide et al., "Fragmentation of cell-free fetal DNA in plasma and urine of pregnant women", Prenat Diagn. Jul. 2005;25(7), www.interscience.wiley.com, Mar. 14, 2005, 604-7.
Kozarewa et al., "Amplification-free Illumina sequencing-library preparation facilitates improved mapping and assembly of GC-biased genomes", Nat. Methods, 6(4), Apr. 2009, 291-295.
Langmead et al., "Ultrafast and memory-efficient alignment of short DNA sequences to the human genome", Genome Biology, vol. 10, 2009, R25.1-R25.10.
Lazinski et al., "Modified Protocol for Illumina Paired-End Library Construction", http://genomics.med.tufts.edu/documents/htseq_protocol_for_illumina_paired.pdf, Feb. 27, 2009, 10.
Leon et al., "Free DNA in the Serum of Cancer Patients and the Effect of Therapy", Cancer Research 37, Mar. 1977, 646-650.
Levy et al., "The Diploid Genome Sequence of an Individual Human", PLoS Biology, vol. 5, Issue 10, Oct. 2007, 2113-2144.
Li et al., "Size Separation of Circulatory DNA in Maternal Plasma Permits Ready Detection of Fetal DNA Polymorphisms", Clin. Chem., vol. 50, No. 6, 2004, 1002-1011.
Liao et al., "Targeted Massively parallel sequencing of maternal plasma DNA permits efficient and unbiased detection of fetal alleles", Clinical Chemistry 57:1, 2011, 92-101.
Liu et al., "Feasibility study of using fetal DNA in maternal plasma for non-invasive prenatal diagnosis", Acta Obstet Gynecol Scand. 86(5), 2007, 535-41.
Lo et al., "Digital PCR for the molecular detection of fetal chromosomal aneuploidy", Proc Natl Acad Sci USA. 104(32), Aug. 7, 2007, 13116-13121.
Lo et al., "Increased fetal DNA concentrations in the plasma of pregnant women carrying fetuses with trisomy 21", Clinical Chemistry 45:10, 1999, 1747-51.
Lo et al., "Maternal Plasma DNA Sequencing Reveals The Genome-Wide Genetic And Mutational Profile Of The Fetus", Sci Transl Med. 2(61):, Dec. 8, 2010, 61ra91.
Lo et al., "Noninvasive prenatal detection of fetal chromosomal aneuploidies by maternal plasma nucleic acid analysis: a review of the current state of the art", BJOG, vol. 116, 2009, 152-157.
Lo et al., "Noninvasive prenatal diagnosis of fetal chromosomal aneuploidies by maternal plasma nucleic acid analysis", Clin Chern. 54(3), Jan. 2008, 461-466.
Lo et al., "Prenatal diagnosis of fetal RhD Status by molecular analysis of maternal plasma", The New England Journal of Medicine, vol. 339, Dec. 10, 1998, 1734-1738.
Lo et al., "Presence of fetal DNA in maternal plasma and serum", Lancet. 350(9076), Aug. 16, 1997, 485-487.
Lo et al., "Quantitative analysis of fetal DNA in maternal plasma and serum implications for noninvasive prenatal diagnosis", Am J Hum Genet 62(4), Apr. 1998, 768-775.
Lo et al., "Rapid Clearance of fetal DNA from Maternal Plasma", Am J Hum Genet. 64(1), 1999, 218-24.
Lun et al., "Microfluidics digital PCR Reveals a Higher than expected fraction of fetal DNA in maternal plasma", Clinical Chemistry, vol. 54, No. 10, Oct. 1, 2008, 1664-1672.
Lun et al., "Noninvasive prenatal diagnosis of monogenic diseases by digital size selection and relative mutation dosage on DNA in maternal plasma", Proceedings of National Academy of Sciences 105(50), 2008, 19920-19925 pp.
Margulies et al., "Genome sequencing in microfabricated high-density picolitre reactors", Nature, vol. 437, 2005, 376-380 and Supplemental Materials.

(56) References Cited

OTHER PUBLICATIONS

Mckernan et al., "Sequence and structural variation in a human genome uncovered by short-read, massively parallel ligation sequencing using two-base encoding", Genome Res. 19(9), Sep. 2009, 1527-41.
Metzker, M.L., "Applications of Next-Generation Sequencing: Sequencing technologies—the next generation", Nature Reviews Genetics, Nature Publishing Group, GB, vol. 11(1), Jan. 1, 2010, 31-46.
Meyerson et al., "Advances in understanding cancer genomes through second-generation sequencing", Nature Reviews Genetics, vol. 11, 2010, 685-696.
Mullighan et al., "Genome-wide profiling of genetic alterations in acute lymphoblastic leukemia: recent insights and future directions.", Leukemia vol. 23, Feb. 26, 2009, 1209-1218.
Nakamoto, "Detection of Microsatellite alterations in Plasma DNA of Malignant Mucosal Melanoma Using Whole Genome Amplification", Bull Tokyo Dent Coll. May 2008; 49(2), May 2008, 77-87.
Nicklas, "A real-time multiplex SNP melting assay to discriminate individuals", J. Forensic Sci. 53(6), Nov. 2008, 1316-24.
Pakstis et al., "Candidate SNPs for a universal individual identification panel", Hum Genet. 121(3-4), May 2007, 305-17.
Pakstis et al., "SNPs for a universal individual identification panel", Hum Genet. 127(3), Mar. 2010, 315-24.
Pandey et al., "Chapter 3 Applied Biosystems SOLID Systems: Ligation-Based Sequencing", Next Generation Genome Sequencing: Towards Personalized Medicine 2008. Edited by Michael Janitz., 2008, 14.
Park et al., "A single-tube protocol for next gen library construction increases complexity and simplifies parallel sample handling", Cancer Research 71(8): Suppl. 1, Abstract No. 4851, Apr. 15, 2011.
Park et al., "Unraveling the Biologic and Clinical Complexities of HER2", Clinical Breast Cancer, vol. 8, Issue 5, Oct. 2008, 392-401.
Pathak et al., "Circulating Cell-Free DNA in Plasma/Serum of Lung Cancer Patients as a Potential Screening and Prognostic Tool", Clin Chem. 52(10):, Oct. 2006, 1833-42.
Pennisi, E., "Semiconductors Inspire New Sequencing Technologies", Science 327, Mar. 5, 2010, 1190.
Pertl et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2011, 1847-1848.
Pheiffer et al., "Polymer-stimulated ligation: enhanced blunt—or cohesive-end ligation of DNA or deoxyribooligonucleotides by T4 DNA ligase in polymer solutions", Nucleic Acids Res.11(22), Nov. 25, 1983, 7853-71.
Pui et al., "Acute lymphoblastic leukaemia", Lancet vol. 371, 2008, 1030-1043.
Pushkarev et al., "Single-molecule sequencing of an individual human genome", Nat Biotechnol. 27(9):, Sep. 2009, 847-50.
Quail et al., "A large genome center's improvements to the Illumina sequencing system", Nature Methods, 5, 2008, 1005-1010.
Redon et al., "Global Variation in copy number in the human genome", Nature 444(7118), 2006, 444-54.
Rygaard et al., "Abnormalities in Structure and Expression of the Retinoblastoma Gene in Small Cell Lung Cancer Cell Lines and Xenografts in Nude Mice", Cancer Res., vol. 50, 1990, 5312-5317.
Sambrook et al., "Molecular Cloning: A Laboratory Manual", Chapter 10, 3rd Edition, Cold Spring Harbor Laboratory, New York, 2001, pp. v-xx.
Santalucia, John Jr., "A unified view of polymer, dumbbell, and oligonucleotide DNA nearest-neighbor thermodynamics", PNAS USA, vol. 95, Feb. 1998, 1460-1465.
Sato et al., "Allelotype of Breast Cancer: Cumulative Allele Losses Promote Tumor Progression in Primary Breast Cancer", Cancer Res., vol. 50, 1990, 7184-7189.
Schwarzenbach et al., "Cell-free Tumor DNA in Blood Plasma As a Marker for Circulating Tumor Cells in Prostate Cancer", Clin Cancer Res. 15(3):, Feb. 1, 2009, 1032-8.
Schwarzenbach et al., "Comparative evaluation of cell-free tumor DNA in blood and disseminated tumor cells in bone marrow of patients with primary breast cancer", Breast Cancer Res. 11(5), 2009, R71.
Sehnert et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011.165910., Apr. 25, 2011, 1042-1049.
Shaikh et al., "High-resolution mapping and analysis of copy number variations in the human genome: A data resource for clinical and research applications", Genome Res., vol. 19, 2009, 1682-1690.
Shendure et al., "Next-generation DNA sequencing", Nature Biotechnology 26(10), 2008, 1135-1145.
Soni et al., "Progress toward Ultrafast DNA Sequencing Using Solid-State Nanopores", Clin Chem, 53(11), 2007, 1996-2001.
Sparks et al., "Non-invasive prenatal detection and selective analysis of cell-free DNA obtained from maternal blood: evaluation for trisomy 21 and trisomy 18", American Journal of Obstetrics and Gynecology; doi: 10.1016/j.ajog.2012.01.030, Jan. 30, 2012, 33 pages.
SS139539, NCBI dbSNP rs131828, Jun. 8, 2000.
SS3206919, NCBI dbSNP rs560681, Sep. 5, 2001.
SS3470339, NCBI dbSNP rs807841, Sep. 24, 2001.
Storchova et al., "The consequences of tetraploidy and aneuploidy", Journal of Cell Science 121 (23), 2008, 3859-3866.
Su et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.
Teixeira et al., "Multiple numerical chromosome aberrations in cancer: what are their causes and what are their consequences?", Seminars in Cancer Biology, vol. 15, Issue 1, Feb. 2005, 3-12.
Thomas et al., "Mechanisms of aneuploidy and its suppression by tumour suppressor proteins", Swiss Med Weekly, 141, 2011, w13170.
Thorstenson et al., "An Automated Hydrodynamic Process for Controlled, Unbiased DNA Shearing", Genome Research 8, 1998, 848-855.
Tong et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Tong et al., "Noninvasive prenatal detection of trisomy 21 by an epigenetic-genetic chromosome-dosage approach", Clin Chem. 56(1), Jan. 2010, 90-8.
Vallone et al., "Demonstration of rapid multiplex PCR amplification involving 16 genetic loci", Forensic Sci Int Genet. 3(1), Dec. 2008, 42-5.
Varmus, H., "The Molecular Genetics of Cellular Oncogenes", Ann Rev Genetics, vol. 18, 1984, 553-612.
Voelkerding et al., "Digital Fetal Aneuploidy Diagnosis by Next-Generation Sequencing", Clin Chem. 56(3), Mar. 2010, 336-8.
Voelkerding et al., "Next-Generation Sequencing: From Basic Research to Diagnostics", Clinical Chemistry 55:4, 2009, 641-658.
Vogelstein, et al., "Digital PCR", PNAS USA, vol. 96, Aug. 3, 1999, 9236-9241.
Walsh et al., "Rare Structural Variants Disrupt Multiple Genes in Neurodevelopmental Pathways in Schizophrenia", Science, vol. 320, 2008, 539-543.
Wheeler et al., "The complete genome of an individual by massively parallel DNA sequencing", Nature. 452(7189), Apr. 17, 2008, 872-6.
Wright et al., "The use of cell-free fetal nucleic acids in maternal blood for non-invasive prenatal diagnosis", Hum Reprod Update. 15(1), Jan. 1, 2009, 139-151.
Yamazawa et al., "Monozygotic female twins for Silver-Russell syndrome and hypomethylation of H19-DMR", J. Human Genetics, vol. 53, 2008, 950-955.

(56) References Cited

OTHER PUBLICATIONS

Zimmerman et al., "Macromolecular crowding allows blunt-end ligation by DNA ligases from rat liver or *Escherichia coli*", Proc Natl Acas Sci USA. 80(19), Oct. 1983, 5852-6.
Chinese Office Action and Search Report for Chinese Application No. 2017106448585, issued by the Chinese Patent Office, Jun. 2, 2020; 17 pgs. including English Translation.
Illumina, "Preparing Sample for Sequencing Genomic DNA," Illumina, Inc., San Diego CA, Mar. 2008, pp. 1-18.
Chinese Office Action and Search Report for Chinese Application No. 201810154581.2, issued by the Chinese Patent Office, Mar. 3, 2021; 7 pgs. including English Translation.
Carter, "Methods and Strategies for analyzing copy number variation using DNA microarrays," *Nature Genetics*, 2007;39:S16-S21.

\* cited by examiner

METHOD FOR DETERMINING COPY NUMBER VARIATIONS

CROSS-REFERENCE

This Application is a continuation of, and claims priority to, U.S. patent application Ser. No. 13/333,832 entitled "Method for Identifying Chromosomal Aneuploidies", filed on Dec. 21, 2011 which is a continuation of U.S. patent application Ser. No. 12/958,352 entitled "Method for Determining Copy Number Variations", which claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; which are incorporated herein by reference in their entirety.

1. FIELD OF THE INVENTION

The invention relates generally to the field of diagnostics, and provides a method for determining variations in the amount of nucleic acid sequences in a mixture of nucleic acids derived from different genomes. In particular, the method is applicable to the practice of noninvasive prenatal diagnostics, and to the diagnosis and monitoring of metastatic progression in cancer patients.

2. BACKGROUND OF THE INVENTION

One of the critical endeavors in human medical research is the discovery of genetic abnormalities that are central to adverse health consequences. In many cases, specific genes and/or critical diagnostic markers have been identified in portions of the genome that are present at abnormal copy numbers. For example, in prenatal diagnosis, extra or missing copies of whole chromosomes are the frequently occurring genetic lesions. In cancer, deletion or multiplication of copies of whole chromosomes or chromosomal segments, and higher level amplifications of specific regions of the genome, are common occurrences.

Most information about copy number variation has been provided by cytogenetic resolution that has permitted recognition of structural abnormalities. Conventional procedures for genetic screening and biological dosimetry have utilized invasive procedures e.g. amniocentesis, to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

The advent of technologies that allow for sequencing entire genomes in relatively short time, and the discovery of circulating cell-free DNA (cfDNA) have provided the opportunity to compare genetic material originating from one chromosome to be compared to that of another without the risks associated with invasive sampling methods. However, the limitations of the existing methods, which include insufficient sensitivity stemming from the limited levels of cfDNA, and the sequencing bias of the technology stemming from the inherent nature of genomic information, underlie the continuing need for noninvasive methods that would provide any or all of the specificity, sensitivity, and applicability, to reliably diagnose copy number changes in a variety of clinical settings.

The present invention fulfills some of the above needs and in particular offers an advantage in providing a reliable method that is applicable at least to the practice of noninvasive prenatal diagnostics, and to the diagnosis and monitoring of metastatic progression in cancer patients.

3. SUMMARY OF THE INVENTION

The invention provides a method for determining copy number variations (CNV) of a sequence of interest in a test sample that comprises a mixture of nucleic acids that are known or are suspected to differ in the amount of one or more sequences of interest. The method comprises a statistical approach that accounts for accrued variability stemming from process-related, interchromosomal, and inter-sequencing variability. The method is applicable to determining CNV of any fetal aneuploidy, and CNVs known or suspected to be associated with a variety of medical conditions.

In one embodiment, the invention provides a method for identifying fetal trisomy 21, said method comprising the steps: (a) obtaining sequence information for a plurality of fetal and maternal nucleic acid molecules of a maternal blood sample e.g. a plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) comprises (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. The at least one normalizing chromosome is a chromosome having the smallest variability and/or the greatest differentiability. The at least one normalizing chromosome is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the group of chromosomes is a group selected from chromosome 9, chromosome 1, chromosome 2, chromosome 11, chromosome 12, and chromosome 14.

In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In another embodiment, the invention provides a method for identifying fetal trisomy 21 in a maternal blood sample e.g. a plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) comprises (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. The at least one normalizing chromosome is a chromosome having the smallest variability and/or the greatest differentiability. The at least one normalizing chromosome is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the group of chromosomes is a group selected from chromosome 9, chromosome 1, chromosome 2, chromosome 11, chromosome 12, and chromosome 14.

In one embodiment, the fetal and maternal nucleic acid molecules are cell-free DNA molecules. In some embodiments, the maternal blood sample is a plasma sample. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In one embodiment, the invention provides a method for identifying fetal trisomy 18, said method comprising the steps: (a) obtaining sequence information for a plurality of fetal and maternal nucleic acid molecules of a maternal blood sample e.g. a plasma sample; (b) using the sequence information to identify a number of mapped sequence tags for chromosome 18; (c) using the sequence information to identify a number of mapped sequence tags for at least one normalizing chromosome; (d) using the number of mapped sequence tags identified for chromosome 18 in step (b) and the number of mapped sequence tags identified for the at least one normalizing chromosome in step (c) to calculate a chromosome dose for chromosome 18; and (e) comparing said chromosome dose to at least one threshold value, and thereby identifying the presence or absence of fetal trisomy 18. In one embodiment, step (d) comprises calculating a chromosome dose for chromosome 18 as the ratio of the number of mapped sequence tags identified for chromosome 18 and the number of mapped sequence tags identified for the at least one normalizing chromosome. Alternatively, step (d) comprises (i) calculating a sequence tag density ratio for chromosome 18, by relating the number of mapped sequence tags identified for chromosome 18 in step (b) to the length of chromosome 18; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 18, wherein the chromosome dose is calculated as the ratio of the sequence tag density ratio for chromosome 18 and the sequence tag density ratio for said at least one normalizing chromosome. The at least one normalizing chromosome is a chromosome having the smallest variability and/or the greatest differentiability. The at least one normalizing chromosome is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected from chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the group of chromosomes is a group selected from chromosome 8, chromosome 2, chromosome 3, chromosome 5, chromosome 6, chromosome 12, and chromosome 14. Preferably, the group of chromosomes is a group selected from chromosome 8, chromosome 2, chromosome 3, chromosome 5, chromosome 6, chromosome 12, and chromosome 14.

In one embodiment, the fetal and maternal nucleic acid molecules are cell-free DNA molecules. In some embodiments, the maternal blood sample is a plasma sample. In some embodiments, the sequencing method for identifying the fetal trisomy 18 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In another embodiment, the invention provides a method for identifying fetal trisomy 18 in a maternal blood sample e.g. a plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 18; (c) using the sequence information to identify a number of mapped sequence tags for at least one normalizing chromosome; (d) using the number of mapped sequence tags identified for chromosome 18 in step (b) and the number of mapped sequence tags identified for the at least one normalizing chromosome in step (c) to calculate a chromosome dose for chromosome 18; and (e) comparing said chromosome dose to at least one threshold value, and thereby identifying the presence or absence of fetal trisomy 18. In one embodiment, step (d) comprises calculating a chromosome dose for chromosome 18 as the ratio of the number of mapped sequence tags identified for chromosome 18 and the number of mapped sequence tags identified for the at least one normalizing chromosome. Alternatively, step (d) comprises (i) calculating a sequence tag density ratio for chromosome 18, by relating the number of mapped sequence tags identified for chromosome 18 in step (b) to the length of chromosome 18; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 18, wherein the chromosome dose is calculated as the ratio of the sequence tag density ratio for chromosome 18 and the sequence tag density ratio for said at least one normalizing chromosome. The at least one normalizing chromosome is a chromosome having the smallest variability and/or the greatest differentiability. The at least one normalizing chromosome is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected from chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the group of chromosomes is a group selected from chromosome 8, chromosome 2, chromosome 3, chromosome 5, chromosome 6, chromosome 12, and chromosome 14.

Preferably, the group of chromosomes is a group selected from chromosome 8, chromosome 2, chromosome 3, chromosome 5, chromosome 6, chromosome 12, and chromosome 14. In one embodiment, the fetal and maternal nucleic acid molecules are cell-free DNA molecules. In some embodiments, the maternal blood sample is a plasma sample. In some embodiments, the sequencing method for identifying the fetal trisomy 18 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In one embodiment, the invention provides a method for identifying fetal trisomy 13, said method comprising the steps: (a) obtaining sequence information for a plurality of fetal and maternal nucleic acid molecules of a maternal blood sample e.g. a plasma sample, (b) using the sequence information to identify a number of mapped sequence tags for chromosome 13; (c) using the sequence information to identify a number of mapped sequence tags for at least one normalizing chromosome; (d) using the number of mapped sequence tags identified for chromosome 13 in step (b) and the number of mapped sequence tags identified for the at least one normalizing chromosome in step (c) to calculate a chromosome dose for chromosome 13; and (e) comparing said chromosome dose to at least one threshold value, and thereby identifying the presence or absence of fetal trisomy 13. In one embodiment, step (d) comprises calculating a chromosome dose for chromosome 13 as the ratio of the number of mapped sequence tags identified for chromosome 13 and the number of mapped sequence tags identified for the at least one normalizing chromosome. Alternatively, step (d) comprises (i) calculating a sequence tag density ratio for chromosome 13, by relating the number of mapped sequence tags identified for chromosome 13 in step (b) to the length of chromosome 13; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 13, wherein the chromosome dose is calculated as the ratio of the sequence tag density ratio for chromosome 13 and the sequence tag density ratio for said at least one normalizing chromosome. The at least one normalizing chromosome is a chromosome having the smallest variability and/or the greatest differentiability. The at least one normalizing chromosome is selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is a chromosome selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the group of chromosomes is a group selected from chromosome 2, chromosome 3, chromosome 4, chromosome 5, chromosome 6, and chromosome 8.

In one embodiment, the fetal and maternal nucleic acid molecules are cell-free DNA molecules. In some embodiments, the maternal blood sample is a plasma sample. In some embodiments, the sequencing method for identifying the fetal trisomy 13 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In another embodiment, the invention provides a method for identifying fetal trisomy 13 in a maternal blood sample e.g. a plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 13; (c) using the sequence information to identify a number of mapped sequence tags for at least one normalizing chromosome; (d) using the number of mapped sequence tags identified for chromosome 13 in step (b) and the number of mapped sequence tags identified for the at least one normalizing chromosome in step (c) to calculate a chromosome dose for chromosome 13; and (e) comparing said chromosome dose to at least one threshold value, and thereby identifying the presence or absence of fetal trisomy 13. In one embodiment, step (d) comprises calculating a chromosome dose for chromosome 13 as the ratio of the number of mapped sequence tags identified for chromosome 13 and the number of mapped sequence tags identified for the at least one normalizing chromosome. Alternatively, step (d) comprises (i) calculating a sequence tag density ratio for chromosome 13, by relating the number of mapped sequence tags identified for chromosome 13 in step (b) to the length of chromosome 13; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 13, wherein the chromosome dose is calculated as the ratio of the sequence tag density ratio for chromosome 13 and the sequence tag density ratio for said at least one normalizing chromosome. The at least one normalizing chromosome is a chromosome having the smallest variability and/or the greatest differentiability. The at least one normalizing chromosome is selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is a chromosome selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the group of chromosomes is a group selected from chromosome 2, chromosome 3, chromosome 4, chromosome 5, chromosome 6, and chromosome 8.

In one embodiment, the fetal and maternal nucleic acid molecules are cell-free DNA molecules. In some embodiments, the maternal blood sample is a plasma sample. In some embodiments, the sequencing method for identifying the fetal trisomy 13 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In one embodiment, the invention provides a method for identifying fetal monosomy X, said method comprising the steps: (a) obtaining sequence information for a plurality of fetal and maternal nucleic acid molecules of a maternal blood sample e.g. a plasma sample; (b) using the sequence information to identify a number of mapped sequence tags for chromosome X; (c) using the sequence information to identify a number of mapped sequence tags for at least one normalizing chromosome; (d) using the number of mapped sequence tags identified for chromosome X in step (b) and the number of mapped sequence tags identified for the at least one normalizing chromosome in step (c) to calculate a chromosome dose for chromosome X; and (e) comparing said chromosome dose to at least one threshold value, and thereby identifying the presence or absence of fetal monosomy X. In one embodiment, step (d) comprises calculating a chromosome dose for chromosome X as the ratio of the number of mapped sequence tags identified for chromosome X and the number of mapped sequence tags identified for the at least one normalizing chromosome. Alternatively, step (d) comprises (i) calculating a sequence tag density ratio for chromosome X, by relating the number of mapped sequence tags identified for chromosome X in step (b) to the length of chromosome X; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome X, wherein the chromosome dose is calculated as the ratio of the sequence tag density ratio for chromosome X and the sequence tag density ratio for said at least one normalizing chromosome. The at least one normalizing chromosome is a chromosome having the smallest variability and/or the greatest differentiability. The at least one normalizing chromosome is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6 and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the group of chromosomes is a group selected from chromosome 2, chromosome 3, chromosome 4, chromosome 5, chromosome 6, and chromosome 8.

In one embodiment, the fetal and maternal nucleic acid molecules are cell-free DNA molecules. In some embodiments, the maternal blood sample is a plasma sample. In some embodiments, the sequencing method for identifying the fetal monosomy X is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In another embodiment, the invention provides a method for identifying fetal monosomy X in a maternal blood sample e.g. a plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome X; (c) using the sequence information to identify a number of mapped sequence tags for at least one normalizing chromosome; (d) using the number of mapped sequence tags identified for chromosome X in step (b) and the number of mapped sequence tags identified for the at least one normalizing chromosome in step (c) to calculate a chromosome dose for chromosome X; and (e) comparing said chromosome dose to at least one threshold value, and thereby identifying the presence or absence of fetal monosomy X. In one embodiment, step (d) comprises calculating a chromosome dose for chromosome X as the ratio of the number of mapped sequence tags identified for chromosome X and the number of mapped sequence tags identified for the at least one normalizing chromosome. Alternatively, step (d) comprises (i) calculating a sequence tag density ratio for chromosome X, by relating the number of mapped sequence tags identified for chromosome X in step (b) to the length of chromosome X; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome X, wherein the chromosome dose is calculated as the ratio of the sequence tag density ratio for chromosome X and the sequence tag density ratio for said at least one normalizing chromosome. The at least one normalizing chromosome is a chromosome having the smallest variability and/or the greatest differentiability. The at least one normalizing chromosome is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6 and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the group of chromosomes is a group selected from chromosome 2, chromosome 3, chromosome 4, chromosome 5, chromosome 6, and chromosome 8.

In one embodiment, the fetal and maternal nucleic acid molecules are cell-free DNA molecules. In some embodiments, the maternal blood sample is a plasma sample. In some embodiments, the sequencing method for identifying the fetal monosomy X is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

In another embodiment, the invention provides a method for identifying copy number variation (CNV) of a sequence of interest e.g. a clinically relevant sequence, in a test sample comprising the steps of: (a) obtaining a test sample and a plurality of qualified samples, said test sample comprising test nucleic acid molecules and said plurality of qualified samples comprising qualified nucleic acid molecules; (b) sequencing at least a portion of said qualified and test nucleic acid molecules, wherein said sequencing comprises providing a plurality of mapped sequence tags for a test and a qualified sequence of interest, and for at least one test and at least one qualified normalizing sequence; (c) based on said sequencing of said qualified nucleic acid molecules, calculating a qualified sequence dose for said qualified sequence of interest in each of said plurality of qualified samples, wherein said calculating a qualified sequence dose comprises determining a parameter for said qualified sequence of interest and at least one qualified normalizing sequence; (d) based on said qualified sequence dose, identifying at least one qualified normalizing sequence, wherein said at least one qualified normalizing sequence has the smallest variability and/or the greatest differentiability in sequence dose in said plurality of qualified samples; (e) based on said sequencing of said nucleic acid molecules in said test sample, calculating a test sequence dose for said test sequence of interest, wherein said calculating a test sequence dose comprises determining a parameter for said test sequence of interest and at least one normalizing test sequence, and wherein said at least one normalizing test sequence corresponds to said at least one qualified normalizing sequence; (f) comparing said test sequence dose to at least one threshold value; and (g) assessing said copy number variation of said sequence of interest in said test sample based on the outcome of step (f). In one embodiment, the parameter for said qualified sequence of interest and at least one qualified normalizing sequence relates the number of sequence tags mapped to said qualified sequence of interest to the number of tags mapped to said qualified normalizing sequence, and wherein said parameter for said test sequence of interest and at least one normalizing test sequence relates the number of sequence tags mapped to said test sequence of interest to the number of tags mapped to said normalizing test sequence. In some embodiments, the sequencing step is performed using next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing. The CNV of a sequence of interest is an aneuploidy, which can be a chromosomal or a partial aneuploidy. In some embodiments, the chromosomal aneuploidy is selected from trisomy 8, trisomy 13, trisomy 15, trisomy 16, trisomy 18, trisomy 21, trisomy 22, monosomy X, and XXX. In other embodiments, the partial aneuploidy is a partial chromosomal deletion or a partial chromosomal insertion. In some embodiments, the CNV identified by the method is a chromosomal or partial aneuploidy associated with cancer. In some embodiments, the test and qualified sample are biological fluid samples e.g. plasma samples, obtained from a pregnant subject such as a pregnant human subject. In other embodiments, a test and qualified biological fluid samples e.g. plasma samples, are obtained from a subject that is known or is suspected of having cancer.

In another embodiment, the invention provides a method for identifying a fetal chromosomal aneuploidy in a test sample, said method comprising: (a) obtaining a test sample comprising a test nucleic acid molecules and a plurality of qualified samples comprising qualified nucleic acid molecules; (b) sequencing at least a portion of said qualified and test nucleic acid molecules, wherein said sequencing comprises providing a plurality of mapped sequence tags for a test and a qualified chromosome of interest, and for at least one test and at least one qualified normalizing chromosome; (c) based on said sequencing of said qualified chromosomes, calculating a qualified chromosome dose for said qualified chromosome of interest in each of said plurality of qualified samples, wherein said calculating a qualified chromosome dose comprises determining a parameter for said qualified chromosome of interest and at least one qualified normalizing chromosome; (d) based on said qualified chromosome dose, identifying at least one qualified normalizing chromosome, wherein said at least one qualified normalizing chromosome has the smallest variability and/or the greatest differentiability in chromosome dose in said plurality of qualified samples; (e) based on said sequencing of said nucleic acid molecules in said test sample, calculating a test chromosome dose for said test chromosome of interest, wherein said calculating a test chromosome dose comprises determining a parameter for said test chromosome of interest and at least one normalizing test chromosome, and wherein said at least one normalizing test chromosome corresponds to said at least one qualified normalizing chromosome; (f) comparing said test chromosome dose to at least one threshold value; and (g) determining said chromosomal aneuploidy based on the outcome of step (f). The parameter for said qualified chromosome of interest and at least one qualified normalizing chromosome relates the number of sequence tags mapped to said qualified chromosome of interest to the number of tags mapped to said normalizing chromosome sequence, and wherein said parameter for said test chromosome of interest and at least one normalizing test chromosome relates the number of sequence tags mapped to said test chromosome of interest to the number of tags mapped to said normalizing chromosome sequence. Chromosomes of interest include but are not limited to chromosome 8, chromosome 13, chromosome 15, chromosome 16, chromosome 18, chromosome 21, chromosome 22, and chromosome X. Chromosomal aneuploidies that can be identified using the method include but are not limited to from trisomy 8, trisomy 13, trisomy 15, trisomy 16, trisomy 18, trisomy 21, trisomy 22, monosomy X, and XXX.

In one embodiment, the test and qualified samples are substantially cell-free biological samples. Biological samples are maternal samples selected from maternal blood, plasma, serum, urine and saliva. In one embodiment, the biological samples are maternal plasma samples. The maternal samples comprise fetal and maternal nucleic acid molecules e.g. cell-free DNA. Sequencing of the fetal and maternal nucleic acid molecules can be performed by next generation sequencing methods. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing.

Although the examples herein concern humans and the language is primarily directed to human concerns, the concept of this invention is applicable to genomes from any plant or animal.

4. INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

5. BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a flowchart of a method 100 for determining the presence or absence of a copy number variation in a test sample comprising a mixture of nucleic acids.

FIGS. 2A and 2B illustrate the distribution of the chromosome dose for chromosome 21 determined from sequencing cfDNA extracted from a set of 48 blood samples obtained from human subjects each pregnant with a male or a female fetus. Chromosome 21 doses for qualified i.e. normal for chromosome 21 (O), and trisomy 21 test samples are shown (Δ) for chromosomes 1-12 and X (FIG. 2A), and for chromosomes 1-22 and X (FIG. 2B).

FIGS. 3A and 3B illustrate the distribution of the chromosome dose for chromosome 18 determined from sequencing cfDNA extracted from a set of 48 blood samples obtained from human subjects each pregnant with a male or a female fetus. Chromosome 18 doses for qualified i.e.

normal for chromosome 18 (O), and trisomy 18 (Δ) test samples are shown for chromosomes 1-12 and X (FIG. 3A), and for chromosomes 1-22 and X (FIG. 3B).

FIGS. 4A and 4B illustrate the distribution of the chromosome dose for chromosome 13 determined from sequencing cfDNA extracted from a set of 48 blood samples obtained from human subjects each pregnant with a male or a female fetus. Chromosome 13 doses for qualified i.e. normal for chromosome 13 (O), and trisomy 13 (Δ) test samples are shown for chromosomes 1-12 and X (FIG. 4A), and for chromosomes 1-22 and X (FIG. 4B).

FIGS. 5A and 5B illustrate the distribution of the chromosome doses for chromosome X determined from sequencing cfDNA extracted from a set of 48 test blood samples obtained from human subjects each pregnant with a male or a female fetus. Chromosome X doses for males (46,XY; (O)), females (46,XX; (Δ)); monosomy X (45,X; (+)), and complex karyotypes (Cplx (X)) samples are shown for chromosomes 1-12 and X (FIG. 5A), and for chromosomes 1-22 and X (FIG. 5B).

FIGS. 6A and 6B illustrate the distribution of the chromosome doses for chromosome Y determined from sequencing cfDNA extracted from a set of 48 test blood samples obtained from human subjects each pregnant with a male or a female fetus. Chromosome Y doses for males (46,XY; (Δ)), females (46,XX; (O)); monosomy X (45,X; (+)), and complex karyotypes (Cplx (X)) samples are shown for chromosomes 1-12 (FIG. 6A), and for chromosomes 1-22 (FIG. 6B).

FIG. 7 shows the coefficient of variation (CV) for chromosomes 21 (■), 18 (●) and 13 (▲) that was determined from the doses shown in FIGS. 2, 3, and 4, respectively.

Figure 10:
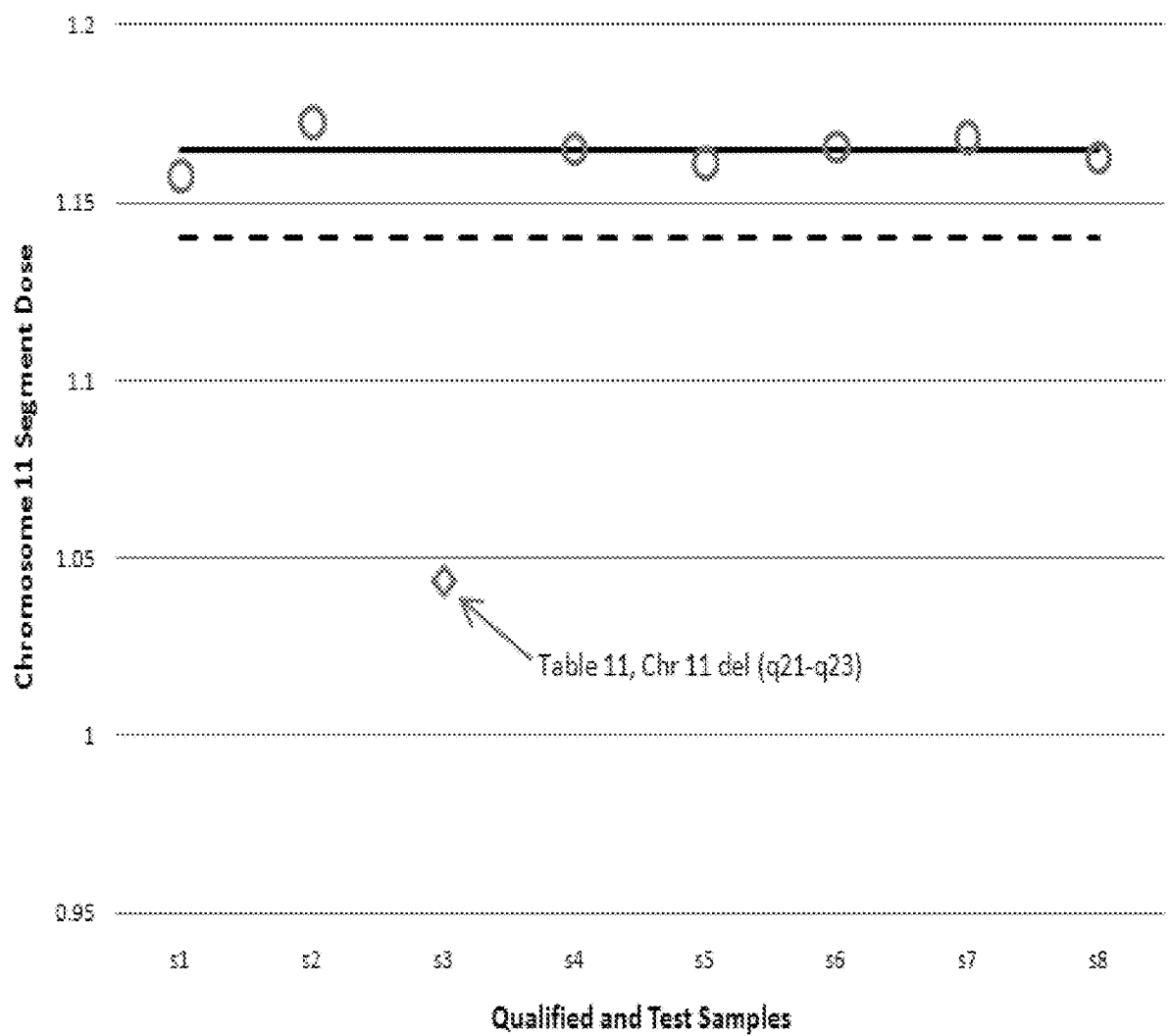

FIG. 10 illustrates the sequence doses (Y-axis) for a segment of chromosome 11 (81000082-103000103 bp) determined from sequencing cfDNA extracted from a set of 7 qualified samples (O) obtained and 1 test sample (♦) from pregnant human subjects. A sample from a subject carrying a fetus with a partial aneuploidy of chromosome 11 (♦) was identified.

FIGS. 11A-11E illustrate the distribution of normalized chromosome doses for chromosome 21 (FIG. 11A), chromosome 18 (FIG. 11B), chromosome 13 (FIG. 11C), chromosome X (FIG. 11D) and chromosome Y (FIG. 11E) relative to the standard deviation of the mean (Y-axis) for the corresponding chromosomes in the unaffected samples.

6. DETAILED DESCRIPTION OF THE INVENTION

The invention provides a method for determining copy number variations (CNV) of a sequence of interest in a test sample that comprises a mixture of nucleic acids that are known or are suspected to differ in the amount of one or more sequence of interest. Sequences of interest include genomic sequences ranging from hundreds of bases to tens of megabases to entire chromosomes that are known or are suspected to be associated with a genetic or a disease condition. Examples of sequences of interest include chromosomes associated with well known aneuploidies e.g. trisomy 21, and segments of chromosomes that are multiplied in diseases such as cancer e.g. partial trisomy 8 in acute myeloid leukemia. The method comprises a statistical approach that accounts for accrued variability stemming from process-related, interchromosomal, and inter-sequencing variability. The method is applicable to determining CNV of any fetal aneuploidy, and CNVs known or suspected to be associated with a variety of medical conditions.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

6.1 Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "assessing" herein refers to characterizing the status of a chromosomal aneuploidy by one of three types of calls: "normal", "affected", and "no-call". For example, in the presence of trisomy the "normal" call is determined by the value of a parameter e.g. a test chromosome dose that is below a user-defined threshold of reliability, the "affected" call is determined by a parameter e.g. a test chromosome dose, that is above a user-defined threshold of reliability, and the "no-call" result is determined by a parameter e.g. a test chromosome dose, that lies between the a user-defined thresholds of reliability for making a "normal" or an "affected" call.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuploidies.

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The term "partial aneuploidy" herein refers to an imbalance of genetic material caused by a loss or gain of part of a chromosome e.g. partial monosomy and partial trisomy, and encompasses imbalances resulting from translocations, deletions and insertions.

The term "plurality" is used herein in reference to a number of nucleic acid molecules or sequence tags that is sufficient to identify significant differences in copy number variations (e.g. chromosome doses) in test samples and qualified samples using in the methods of the invention. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "portion" is used herein in reference to the amount of sequence information of fetal and maternal nucleic acid molecules in a biological sample that in sum amount to less than the sequence information of <1 human genome.

The term "test sample" herein refers to a sample comprising a mixture of nucleic acids comprising at least one nucleic acid sequence whose copy number is suspected of having undergone variation. Nucleic acids present in a test sample are referred to as "test nucleic acids".

The term "qualified sample" herein refers to a sample comprising a mixture of nucleic acids that are present in a known copy number to which the nucleic acids in a test sample are compared, and it is a sample that is normal i.e. not aneuploid, for the sequence of interest e.g. a qualified sample used for identifying a normalizing chromosome for chromosome 21 is a sample that is not a trisomy 21 sample.

The term "qualified nucleic acid" is used interchangeably with "qualified sequence" is a sequence against which the amount of a test sequence or test nucleic acid is compared. A qualified sequence is one present in a biological sample preferably at a known representation i.e. the amount of a qualified sequence is known. A "qualified sequence of interest" is a qualified sequence for which the amount is known in a qualified sample, and is a sequence that is associated with a difference in sequence representation in an individual with a medical condition.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may also be a portion of a chromosome, or a chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "normalizing sequence" herein refers to a sequence that displays a variability in the number of sequence tags that are mapped to it among samples and sequencing runs that best approximates that of the sequence of interest for which it is used as a normalizing parameter, and that can best differentiate an affected sample from one or more unaffected samples. A "normalizing chromosome" is an example of a "normalizing sequence".

The term "differentiability" herein refers to the characteristic of a normalizing chromosome that enables to distinguish one or more unaffected i.e. normal, samples from one or more affected i.e. aneuploid, samples.

The term "sequence dose" herein refers to a parameter that relates the sequence tag density of a sequence of interest to the tag density of a normalizing sequence. A "test sequence dose" is a parameter that relates the sequence tag density of a sequence of interest e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The term "parameter" herein refers to a numerical value that characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention, a subject can be diagnosed with a copy number variation e.g. trisomy 21.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

As used herein, the terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

As used herein, the term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information available on the worldwide web at ncbi.nlm.nih.gov. A "genome" refers to the complete genetic information of an organism or virus, expressed in nucleic acid sequences.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids e.g. cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "mixed sample" herein refers to a sample containing a mixture of nucleic acids, which are derived from different genomes.

The term "maternal sample" herein refers to a biological sample obtained from a pregnant subject e.g. a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "corresponding to" refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

As used herein, the term "substantially cell free" encompasses preparations of the desired sample from which components that are normally associated with it are removed. For example, a plasma sample is rendered essentially cell free by removing blood cells e.g. red cells, which are normally associated with it. In some embodiments, substantially free samples are processed to remove cells that would otherwise contribute to the desired genetic material that is to be tested for a CNV.

As used herein, the term "fetal fraction" refers to the fraction of fetal nucleic acids present in a sample comprising fetal and maternal nucleic acid.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs e.g. provided in the NCBI36/hg18 assembly of the human chromosome found on the world wide web at genome.ucsc.edu/cgi-bin/hgTracks?hgsid=167155613&chromInfoPage=

The term "subject" herein refers to a human subject as well as a non-human subject such as a mammal, an invertebrate, a vertebrate, a fungus, a yeast, a bacteria, and a virus. Although the examples herein concern humans and the language is primarily directed to human concerns, the concept of this invention is applicable to genomes from any plant or animal, and is useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

6.2 Description

The invention provides a method for determining copy number variations (CNV) of a sequence of interest in a test sample that comprises a mixture of nucleic acids derived from two different genomes, and which are known or are suspected to differ in the amount of one or more sequence of interest. Copy number variations determined by the method of the invention include gains or losses of entire chromosomes, alterations involving very large chromosomal segments that are microscopically visible, and an abundance of sub-microscopic copy number variation of DNA segments ranging from kilobases (kb) to megabases (Mb) in size.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316: 445-449 [2007]; Walsh et al., Science 320:539-543 [2008]). CNV arise from genomic rearrangements, primarily owing to deletion, duplication, insertion, and unbalanced translocation events.

In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital PCR concept of counting cell-free DNA molecules (Fan et al., Proc Natl Acad Sci USA 105:16266-16271 [2008]; Chiu et al., Proc Natl Acad Sci USA 2008; 105: 20458-20463 [2008]). The sequencing technologies of NGS include pyrosequencing, sequencing-by-synthesis with reversible dye terminators, sequencing by oligonucleotide probe ligation and real time sequencing Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology. Sanger sequencing including the automated Sanger sequencing, can also be employed by the method of the invention. Additional sequencing methods that comprise the use of developing nucleic acid imaging technologies e.g. atomic force microscopy (AFM) or transmission electron microscopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are identified by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In one embodiment, the DNA sequencing technology that is used in the method of the invention is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated.

In one embodiment, the DNA sequencing technology that is used in the method of the invention is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18& hgsid=166260105). Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the method described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads e.g. 36 bp, are obtained from mapping the reads to the reference genome per sample. In one embodiment, all the sequence reads are mapped to all regions of the reference genome. In one embodiment, the tags that have been mapped to all regions e.g. all chromosomes, of the reference genome are counted, and the CNV i.e. the over- or under-representation of a sequence of interest e.g. a chromosome or portion thereof, in the mixed DNA sample is determined. The method does not require differentiation between the two genomes.

The accuracy required for correctly determining whether a CNV e.g. aneuploidy, is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. The present method uses chromosome doses based on the knowledge of normalizing chromosomes, to intrinsically account for the accrued variability stemming from interchromosomal, inter-sequencing and platform-dependent variability.

Figure 1:
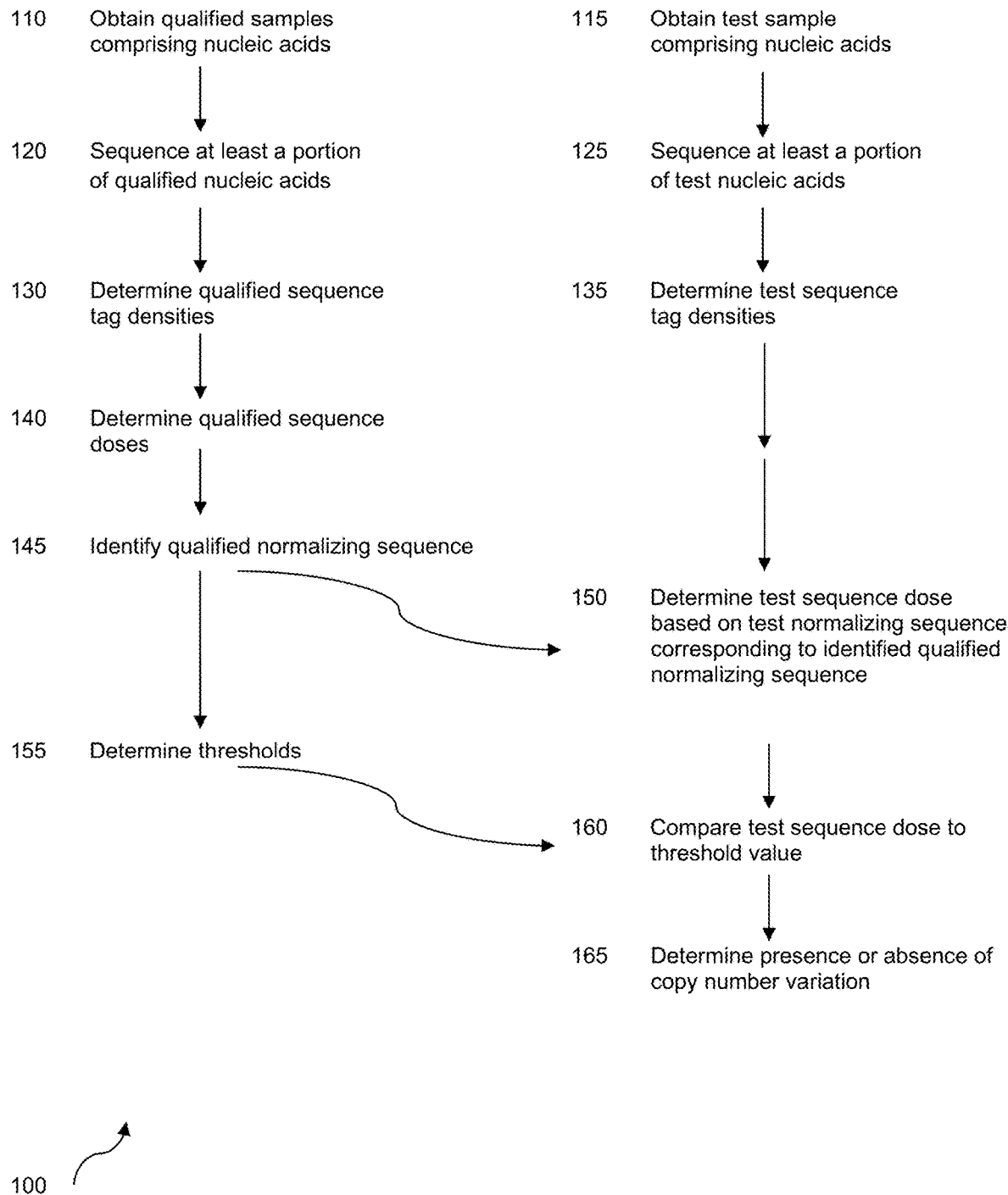
Figure 2A:
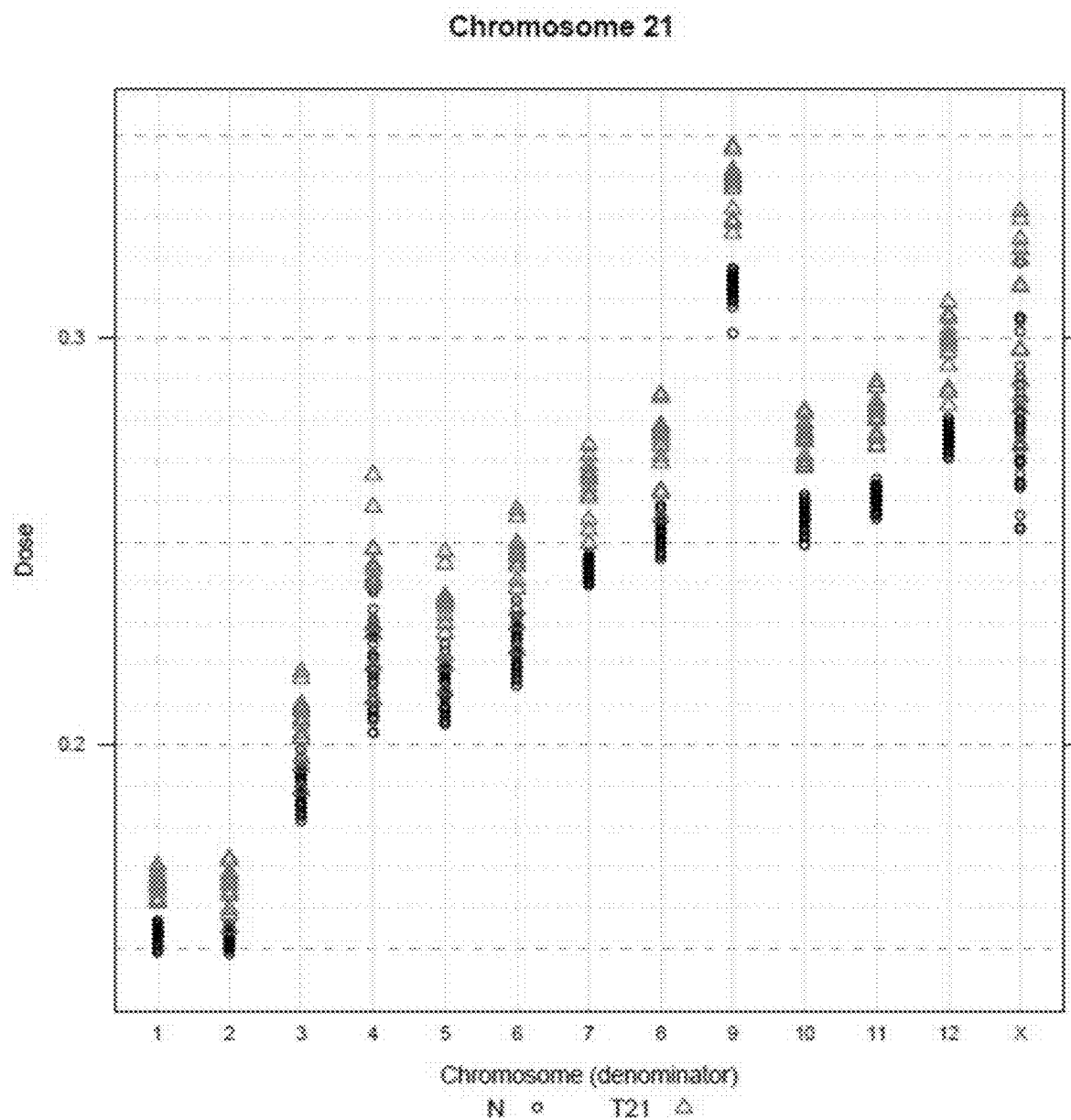
Figure 2B:
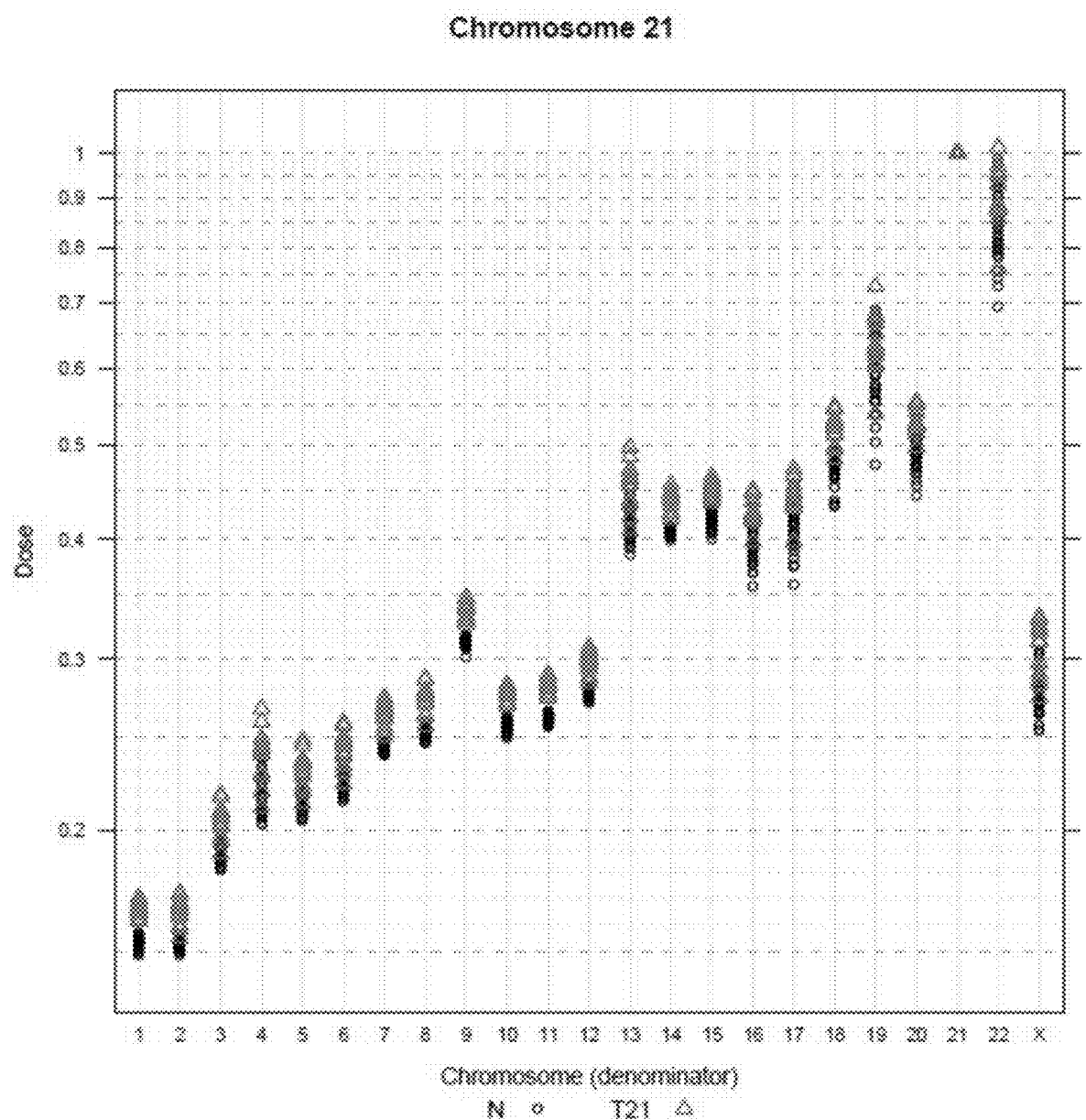
Figure 3A:
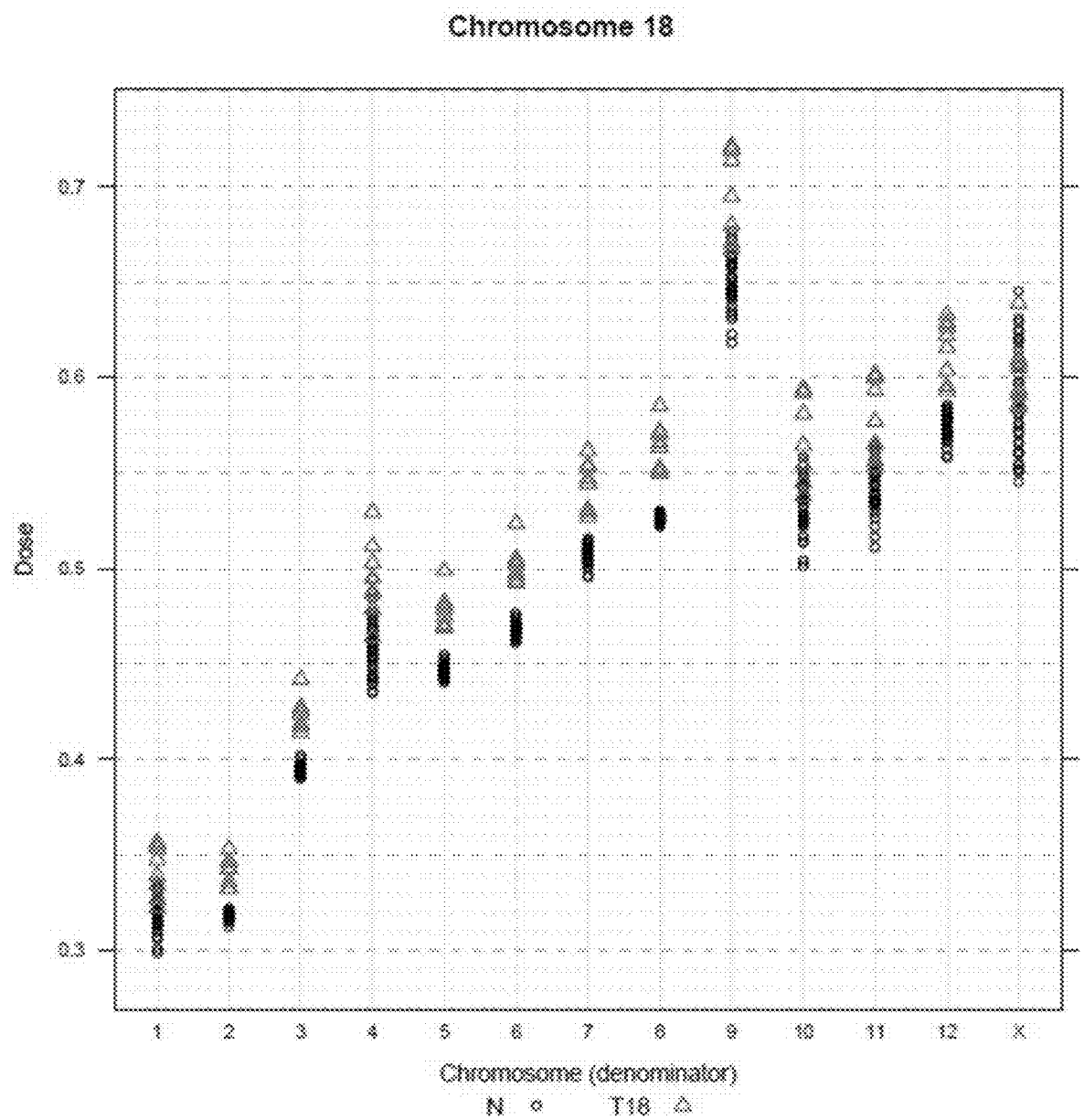
Figure 3B:
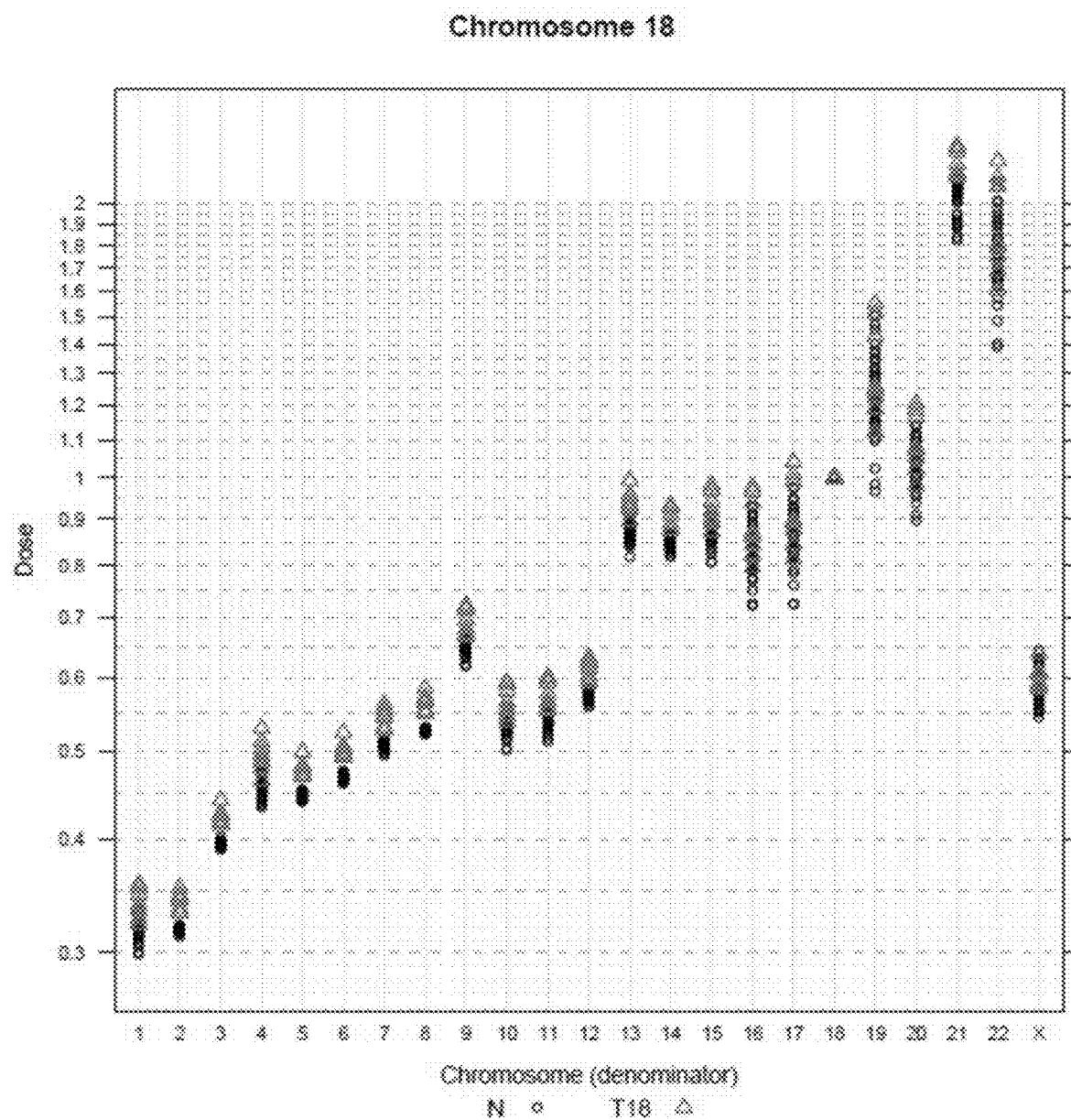
Figure 4A:
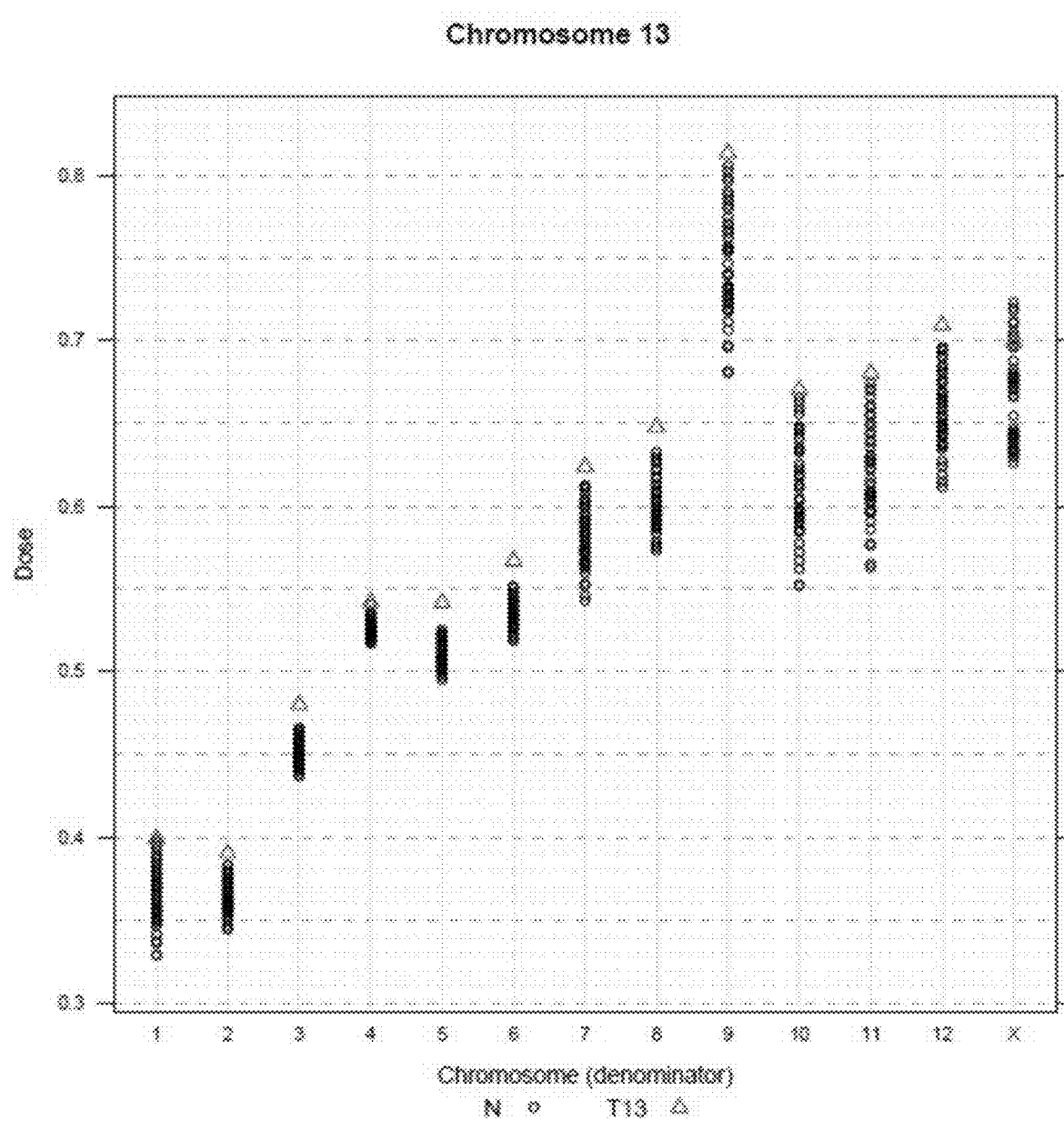
Figure 4B:
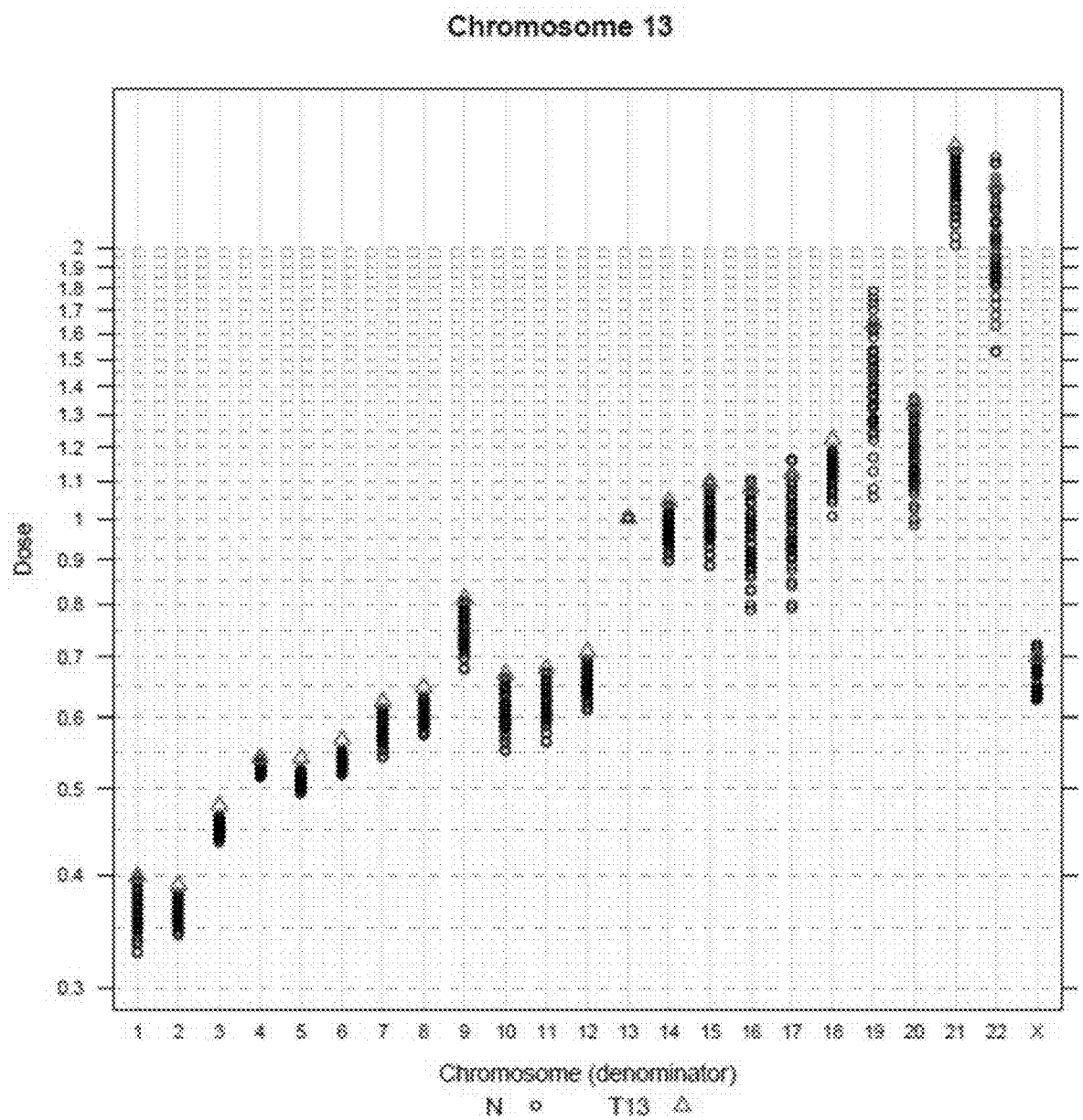
Figure 5A:
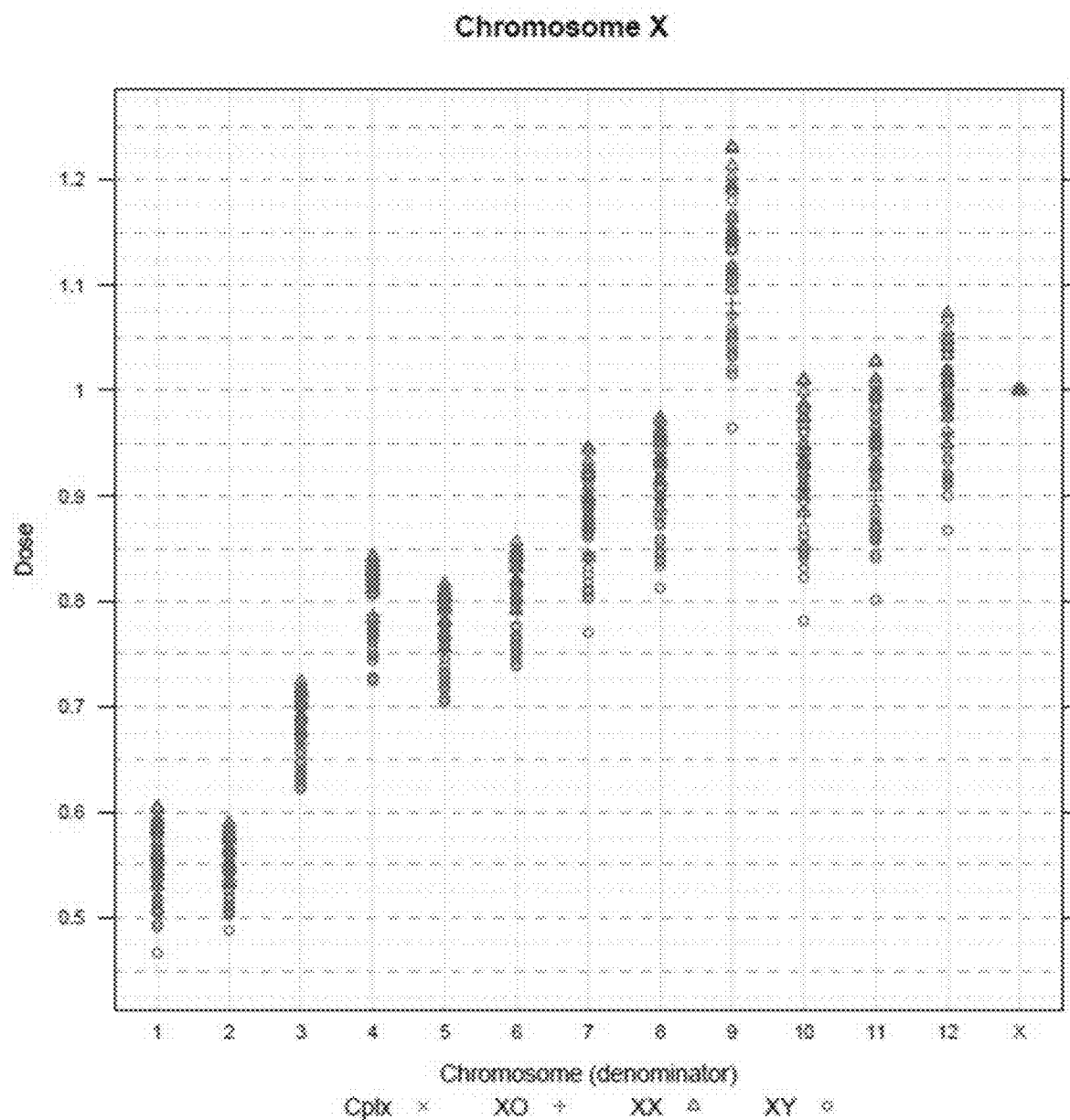
Figure 5B:
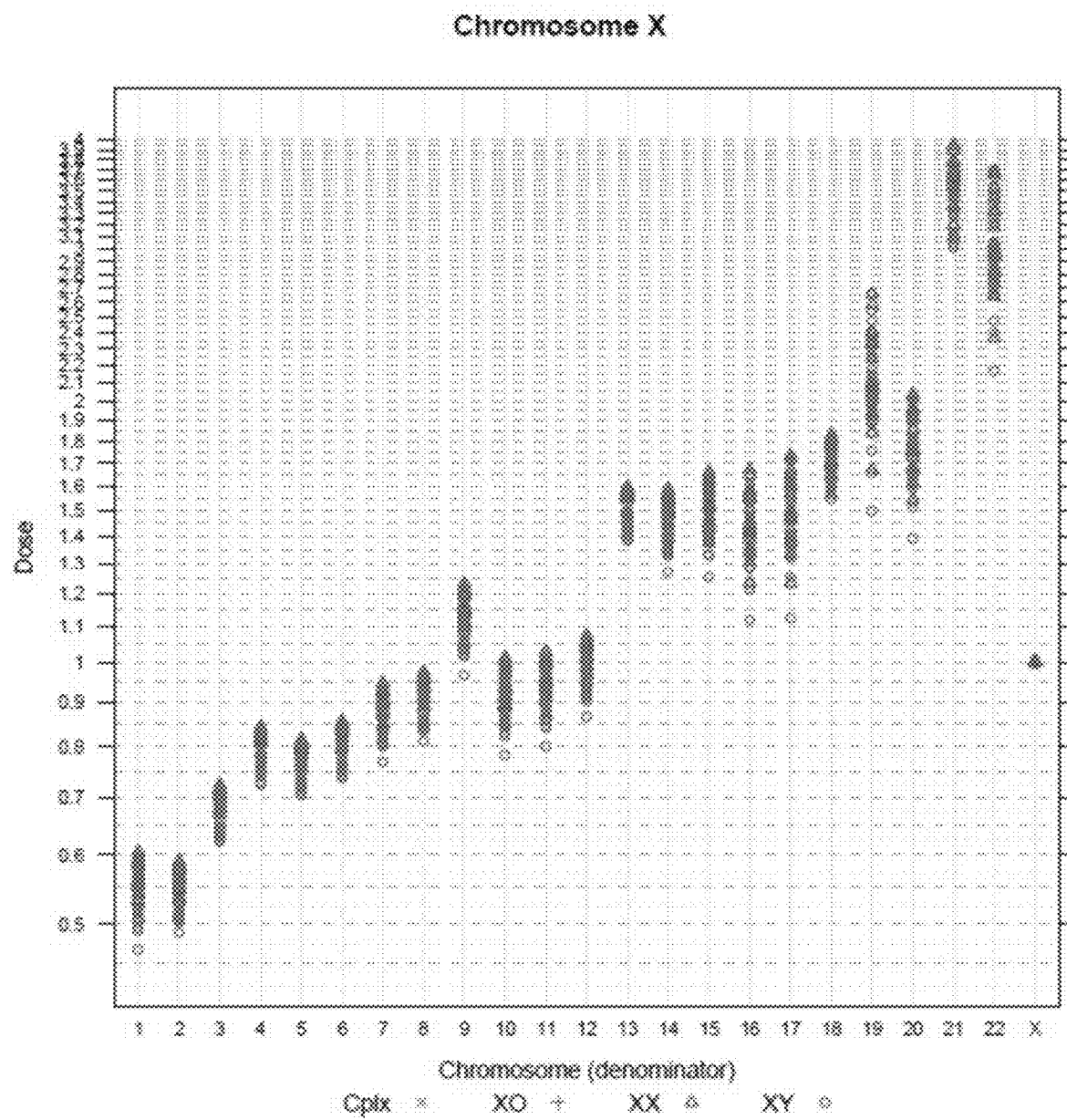
Figure 6A:
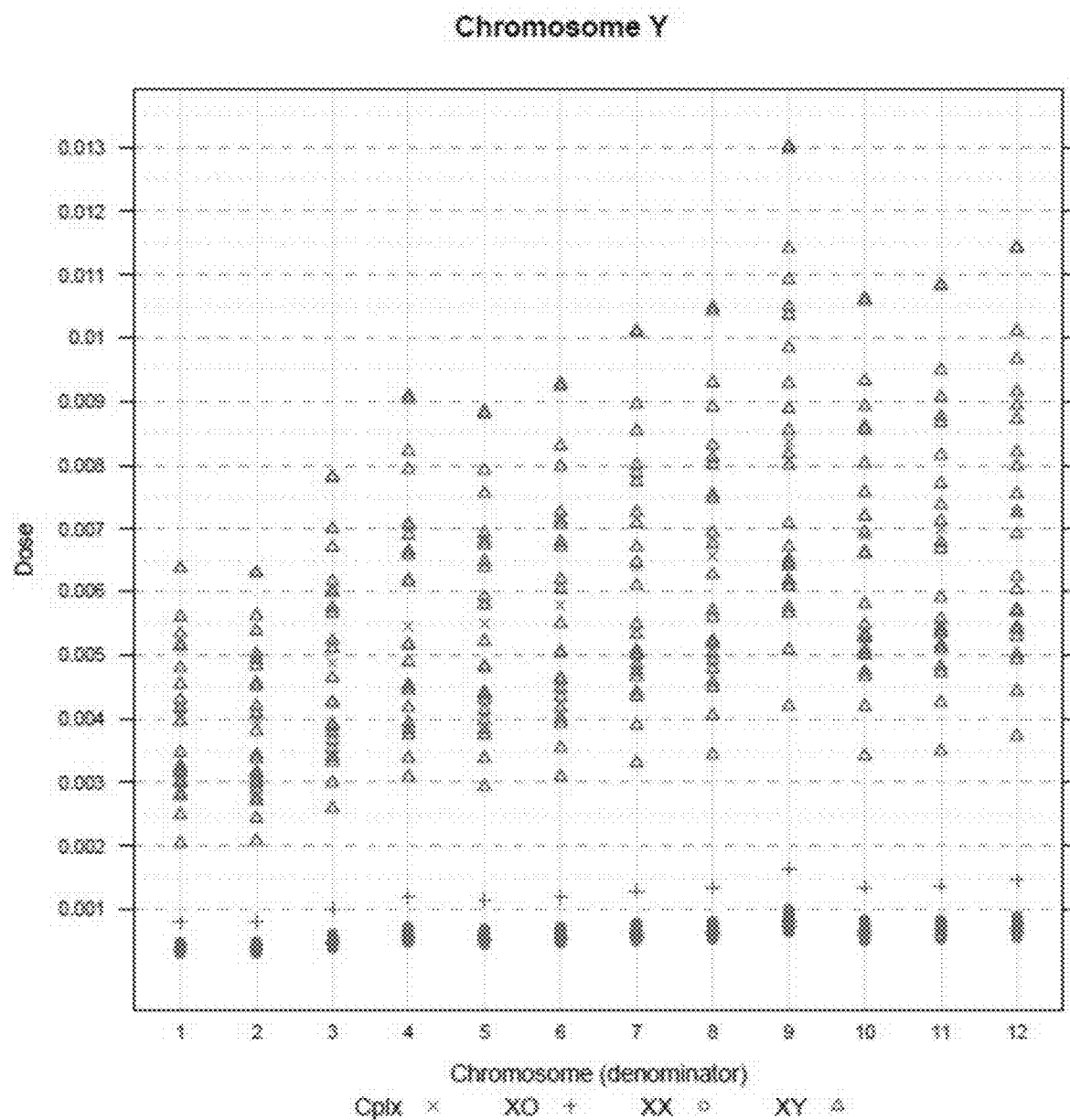
Figure 6B:
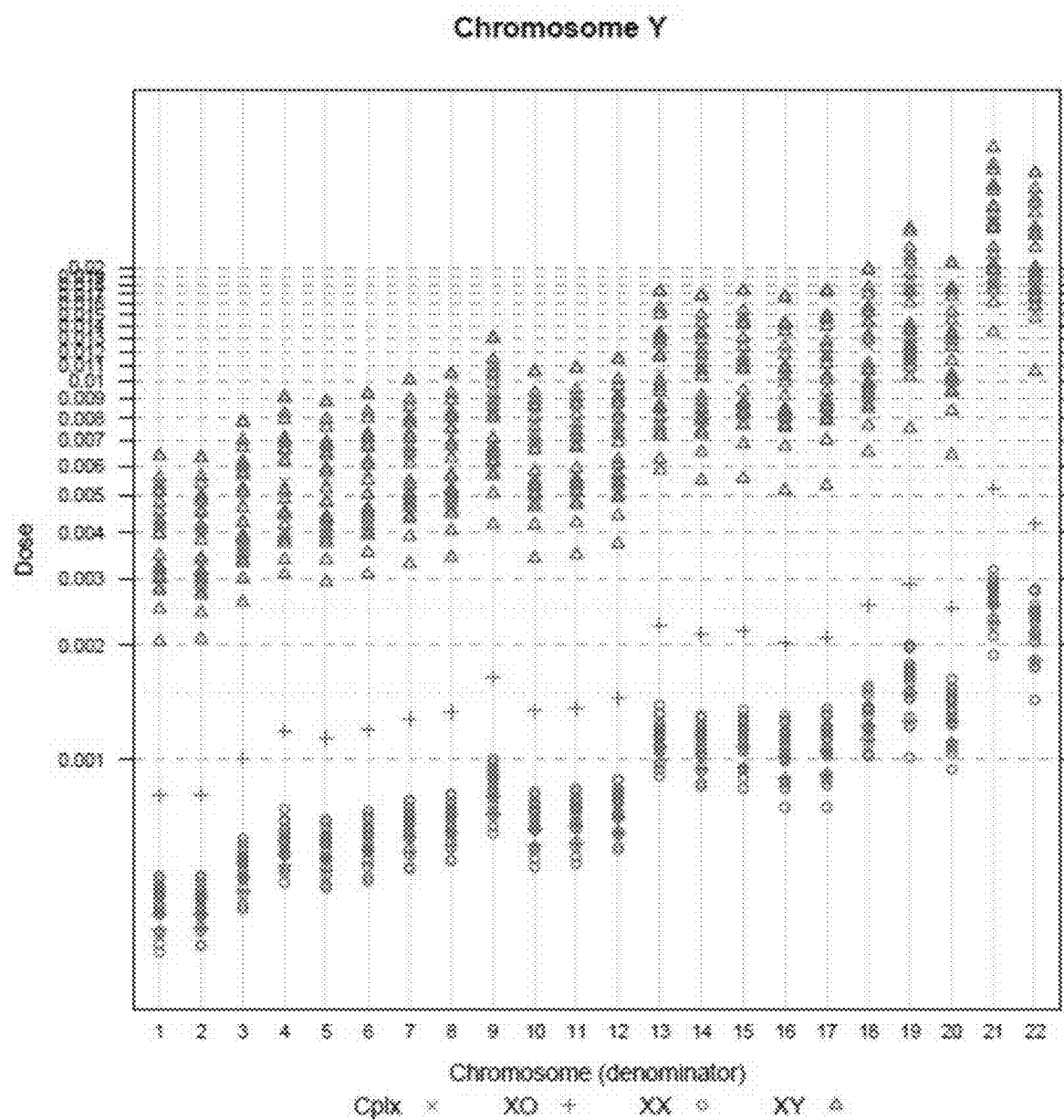

FIG. 1 provides a flow diagram of an embodiment of method of the invention 100 for determining a CNV of a sequence of interest in a biological sample. In some embodiments, a biological sample is obtained from a subject and comprises a mixture of nucleic acids contributed by different genomes. The different genomes can be contributed to the sample by two individuals e.g. the different genomes are contributed by the fetus and the mother carrying the fetus. Alternatively, the genomes are contributed to the sample by aneuploid cancerous cells and normal euploid cells from the same subject e.g. a plasma sample from a cancer patient.

A set of qualified samples is obtained to identify qualified normalizing sequences and to provide variance values for use in determining statistically meaningful identification of CNV in test samples. In step 110, a plurality of biological qualified samples are obtained from a plurality of subjects known to comprise cells having a normal copy number for any one sequence of interest. In one embodiment, the qualified samples are obtained from mothers pregnant with a fetus that has been confirmed using cytogenetic means to have a normal copy number of chromosomes. The biological qualified samples may be a biological fluid e.g. plasma, or any suitable sample as described below. In some embodiments, a qualified sample contains a mixture of nucleic acid molecules e.g. cfDNA molecules. In some embodiments, the qualified sample is a maternal plasma sample that contains a mixture of fetal and maternal cfDNA molecules.

In step 120, at least a portion of each of all the qualified nucleic acids contained in the qualified samples are sequenced to generate sequence reads e.g. 36 bp reads, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence reads comprise 36 bp. Sequence reads are aligned to a reference genome, and the reads that are uniquely mapped to the reference genome are known as sequence tags. In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to a reference genome.

In step 130, all the tags obtained from sequencing the nucleic acids in the qualified samples are counted to determine a qualified sequence tag density. In one embodiment the sequence tag density is determined as the number of qualified sequence tags mapped to the sequence of interest on the reference genome. In another embodiment, the qualified sequence tag density is determined as the number of qualified sequence tags mapped to a sequence of interest normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the sequence tag density for a sequence of interest e.g. a clinically-relevant sequence, in the qualified samples is determined, as are the sequence tag densities for additional sequences from which normalizing sequences are identified subsequently. In one embodiment, the sequence of interest is a chromosome that is associated with a chromosomal aneuploidy e.g. chromosome 21, and the qualified normalizing sequence is a chromosome that is not associated with a chromosomal aneuploidy and whose variation in sequence tag density best approximates that of chromosome 21. For example, a qualified normalizing sequence is a sequence that has the smallest variability. In some embodiments, the normalizing sequence is a sequence that best distinguishes one or more qualified, samples from one or more affected samples i.e. the normalizing sequence is a sequence that has the greatest differentiability. In other embodiments, the normalizing sequence is a sequence that has the smallest variability and the greatest differentiability. The level of differentiability can be determined as a statistical difference between the chromosome doses in a population of qualified samples and the chromosome dose(s) in one or more test samples.

In another embodiment, the sequence of interest is a segment of a chromosome associated with a partial aneuploidy, e.g. a chromosomal deletion or insertion, or unbalanced chromosomal translocation, and the normalizing sequence is a chromosomal segment that is not associated with the partial aneuploidy and whose variation in sequence tag density best approximates that of the chromosome segment associated with the partial aneuploidy.

In step 140, based on the calculated qualified tag densities, a qualified sequence dose for a sequence of interest is determined as the ratio of the sequence tag density for the sequence of interest and the qualified sequence tag density for additional sequences from which normalizing sequences are identified subsequently. In one embodiment, doses for the chromosome of interest e.g. chromosome 21, is determined as a ratio of the sequence tag density of chromosome 21 and the sequence tag density for each of all the remaining chromosomes i.e. chromosomes 1-20, chromosome 22, chromosome X, and chromosome Y.

In step 145, a normalizing sequence is identified for a sequence of interest in a qualified sample based on the calculated sequence doses. The method identifies sequences that inherently have similar characteristics and that are prone to similar variations among samples and sequencing runs, and which are useful for determining sequence doses in test samples. In some embodiments, more than one normalizing sequence is identified. For example, the variation e.g. coefficient of variation, in chromosome dose for chromosome of interest 21 is least when the sequence tag density of chromosome 14 is used. In other embodiments, two, three, four, five, six, seven, eight or more normalizing sequences are identified for use in determining a sequence dose for a sequence of interest in a test sample. In one embodiment, the normalizing sequence for chromosome 21 is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the group of chromosomes is a group selected from chromosome 9, chromosome 1, chromosome 2, chromosome 11, chromosome 12, and chromosome 14.

In one embodiment, the normalizing sequence for chromosome 18 is selected chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected from chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the group of chromosomes is a group selected from chromosome 8, chromosome 2, chromosome 3, chromosome 5, chromosome 6, chromosome 12, and chromosome 14.

In one embodiment, the normalizing sequence for chromosome X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6 and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the group of chromosomes is a group selected from chromosome 2, chromosome 3, chromosome 4, chromosome 5, chromosome 6, and chromosome 8.

In one embodiment, the normalizing sequence for chromosome 13 is a chromosome selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is a chromosome selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the group of chromosomes is a group selected from chromosome 2, chromosome 3, chromosome 4, chromosome 5, chromosome 6, and chromosome 8.

The variation in chromosome dose for chromosome Y is greater than 30 independently of which normalizing chromosome is used in determining the chromosome Y dose. Therefore, any one chromosome, or a group of two or more chromosomes selected from chromosomes 1-22 and chromosome X can be used as the normalizing sequence for chromosome Y. In one embodiment, the at least one normalizing chromosome is a group of chromosomes consisting of chromosomes 1-22, and chromosome X. In another embodiment, the group of chromosomes consists of chromosome 2, chromosome 3, chromosome 4, chromosome 5, and chromosome 6.

Based on the identification of the normalizing sequence(s) in qualified samples, a sequence dose is determined for a sequence of interest in a test sample comprising a mixture of nucleic acids derived from genomes that differ in one or more sequences of interest.

In step 115, a test sample is obtained from a subject suspected or known to carry a clinically-relevant CNV of a sequence of interest. The test sample may be a biological fluid e.g. plasma, or any suitable sample as described below. In some embodiments, a test sample contains a mixture of nucleic acid molecules e.g. cfDNA molecules. In some embodiments, the test sample is a maternal plasma sample that contains a mixture of fetal and maternal cfDNA molecules.

In step 125, at least a portion of the test nucleic acids in the test sample is sequenced to generate millions of sequence reads comprising between 20 and 500 bp e.g. 36 bp. As in step 120, the reads generated from sequencing the nucleic acids in the test sample are uniquely mapped to a reference genome. As described in step 120, at least about $3\times10^6$ qualified sequence lags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome.

In step 135, all the tags obtained from sequencing the nucleic acids in the test samples are counted to determine a test sequence tag density. In one embodiment, the number of test sequence tags mapped to a sequence of interest is normalized to the known length of a sequence of interest to which they are mapped to provide a test sequence tag density ratio. As described for the qualified samples, normalization to the known length of a sequence of interest is not required, and may be included as a step to reduce the number of digits in a number to simplify it for human interpretation. As all the mapped test sequence tags are counted in the test sample, the sequence tag density for a sequence of interest e.g. a clinically-relevant sequence, in the test samples is determined, as are the sequence tag densities for additional sequences that correspond to at least one normalizing sequence identified in the qualified samples.

In step 150, based on the identity of at least one normalizing sequence in the qualified samples, a test sequence dose is determined for a sequence of interest in the test sample. The sequence dose for a sequence of interest in a test sample is a ratio of the sequence tag density determined for the sequence of interest in the test sample and the sequence tag density of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be chromosome 14, then the test sequence dose for chromosome 21 (sequence of interest) is determined as the ratio of the sequence tag density for chromosome 21 in and the sequence tag density for chromosome 14 each determined in the test sample. Similarly, chromosome doses for chromosomes 13, 18, X, Y, and other chromosomes associated with chromosomal aneuploidies are determined. As described previously, a sequence of interest can be part of a chromosome e.g. a chromosome segment. Accordingly, the dose for a chromosome segment can be determined as the ratio of the sequence tag density determined for the segment in the test sample and the sequence tag density for the normalizing chromosome segment in the test sample, wherein the normalizing segment in the test sample corresponds to the normalizing segment identified in the qualified samples for the particular segment of interest.

In step 155, threshold values are derived from standard deviation values established for a plurality of qualified sequence doses. Accurate classification depends on the differences between probability distributions for the different classes i.e. type of aneuploidy. Preferably, thresholds are chosen from empirical distribution for each type of aneuploidy e.g. trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids.

In step 160, the copy number variation of the sequence of interest is determined in the test sample by comparing the test sequence dose for the sequence of interest to at least one threshold value established from the qualified sequence doses.

In step 165, the calculated dose for a test sequence of interest is compared to that set as the threshold values that are chosen according to a user-defined threshold of reliability to classify the sample as a "normal" an "affected" or a "no call". The "no call" samples are samples for which a definitive diagnosis cannot be made with reliability.

Another embodiment of the invention provides a method for providing prenatal diagnosis of a fetal chromosomal aneuploidy in a biological sample comprising fetal and maternal nucleic acid molecules. The diagnosis is made based on receiving the data from sequencing at least a portion of the mixture of the fetal and maternal nucleic acid molecules derived from a biological test sample e.g. a maternal plasma sample, computing from the sequencing data a normalizing chromosome dose for one or more chromosomes of interest, determining a statistically significant difference between the normalizing chromosome dose for the chromosome of interest in the test sample and a threshold value established in a plurality of qualified (normal) samples, and providing the prenatal diagnosis based on the statistical difference. As described in step 165 of the method, a diagnosis of normal or affected is made. A "no call" is provided in the event that the diagnosis for normal or affected cannot be made with confidence.

Samples

Samples that are used for determining a CNV e.g. chromosomal and partial aneuploidies, comprise nucleic acids that are present in cells or that are "cell-free". In some embodiments of the invention it is advantageous to obtain cell-free nucleic acids e.g. cell-free DNA (cfDNA). Cell-free nucleic acids, including cell-free DNA, can be obtained by various methods known in the art from biological samples including but not limited to plasma and serum (Chen et al., Nature Med. 2: 1033-1035 [1996]; Lo et al., Lancet 350: 485-487 [1997]). To separate cell-free DNA from cells, fractionation, centrifugation (e.g., density gradient centrifugation), DNA-specific precipitation, or high-throughput cell sorting and/or separation methods can be used. Examples of methods for processing fluid samples have been previously disclosed, e.g., U.S. Patent Application Nos. 20050282293, 20050224351, and 20050065735.

The sample comprising the mixture of nucleic acids to which the methods described herein are applied is a biological sample such as a tissue sample, a biological fluid sample, or a cell sample. In some embodiments, the mixture of nucleic acids is purified or isolated from the biological sample by any one of the known methods. A sample can consist of purified or isolated polynucleotide, or it can comprise a biological sample such as a tissue sample, a biological fluid sample, or a cell sample. A biological fluid includes, as non-limiting examples, blood, plasma, serum, sweat, tears, sputum, urine, sputum, car flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the sample is a sample that is easily obtainable by non-invasive procedures e.g. blood, plasma, serum, sweat, tears, sputum, urine, sputum, ear flow, and saliva. Preferably, the biological sample is a peripheral blood sample, or the plasma and serum fractions. In other embodiments, the biological sample is a swab or smear, a biopsy specimen, or a cell culture. In another embodiment, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, or individuals with exposure to an infectious disease agent (e.g., HIV).

In one embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and serum fractions. In other embodiments, the biological sample is a swab or smear, a biopsy specimen, or a cell culture. In another embodiment, the maternal sample is a mixture of two or more biological samples e.g. a biological sample can comprise two or more of a biological fluid sample, a tissue sample, and a cell culture sample. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

Methods of isolating nucleic acids from biological sources are well known and will differ depending upon the nature of the source. One of skill in the art can readily isolate nucleic acid from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

Determination of CNV for Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely. DS can be cause by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. The method of the invention can be used to diagnose these and other chromosomal abnormalities prenatally.

According to embodiments of the present invention the trisomy determined by the present invention is selected from trisomy 21 (T21; Down Syndrome), trisomy 18 (T18; Edward's Syndrome), trisomy 16 (T16), trisomy 22 (T22; Cat Eye Syndrome), trisomy 15 (T15; Prader Willi Syndrome), trisomy 13 (T13; Patau Syndrome), trisomy 8 (T8; Warkany Syndrome) and the XXY (Kleinefelter Syndrome), XYY, or XXX trisomies. It will be appreciated that various other trisomies and partial trisomies can be determined in fetal cfDNA according to the teachings of the present invention. These include, but not limited to, partial trisomy 1q32-44, trisomy 9 p with trisomy, trisomy 4 mosaicism, trisomy 17p, partial trisomy 4q26-qter, trisomy 9, partial 2p trisomy, partial trisomy 1q, and/or partial trisomy 6p/monosomy 6q.

The method of the present invention can be also used to determine chromosomal monosomy X, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method of the invention. Monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia. In one embodiment, the method of the invention is used to determine partial monosomies including but not limited to monosomy 18p, partial monosomy of chromosome 15 (15q11-q13), partial monosomy 13q, and partial monosomy of chromosome 22 can also be determined using the method.

The method of the invention can be also used to determine any aneuploidy if one of the parents is a known carrier of such abnormality. These include, but not limited to, mosaic for a small supernumerary marker chromosome (SMC); t(11;14)(p15;p13) translocation; unbalanced translocation t(8;11)(p23.2;p15.5); 11q23 microdeletion; Smith-Magenis syndrome 17p11.2 deletion; 22q13.3 deletion; Xp22.3 microdeletion; 10p14 deletion; 20p microdeletion, DiGeorge syndrome [del(22)q11.2q11.23)], Williams syndrome (7q11.23 and 7q36 deletions); 1p36 deletion; 2p microdeletion; neurofibromatosis type 1 (17q11.2 microdeletion), Yq deletion; Wolf-Hirschhorn syndrome (WHS; 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p11.2 deletion; and 2q37 microdeletion.

Determination of CNV of Clinical Disorders

In addition to the early determination of birth defects, the methods described herein can be applied to the determination of any abnormality in the representation of genetic sequences within the genome. It has been shown that blood plasma and serum DNA from cancer patients contains measurable quantities of tumor DNA, which can be recovered and used as surrogate source of tumor DNA. Tumors are characterized by aneuploidy, or inappropriate numbers of gene sequences or even entire chromosomes. The determination of a difference in the amount of a given sequence i.e. a sequence of interest, in a sample from an individual can thus be used in the diagnosis of a medical condition e.g. cancer.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. [Sato et al., Cancer Res., 50: 7184-7189 [1990]; Jongsma et al., J Clin PAthol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the invention assesses CNV of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processes) from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990]) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Kmx20 and the cytoskeletal remodeling protein, alpha-catenin (Eisenmann et al., Oncogene 28:3429-3441 [2009]). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagus, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In one embodiment, the method provides a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by the method can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, $p185^{HER2}$).

The method can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

Apparatus and Systems for Determining CNV

Analysis of the sequencing data and the diagnosis derived therefrom are typically performed using various computer algorithms and programs. In one embodiment, the invention provides a computer program product for generating an output indicating the presence or absence of a fetal aneuploidy in a test sample. The computer product comprises a computer readable medium having a computer executable logic recorded thereon for enabling a processor to diagnose a fetal aneuploidy comprising: a receiving procedure for receiving sequencing data from at least a portion of nucleic acid molecules from a maternal biological sample, wherein said sequencing data comprises a calculated chromosome; computer assisted logic for analyzing a fetal aneuploidy from said received data; and an output procedure for generating an output indicating the presence, absence or kind of said fetal aneuploidy. The method of the invention can be performed using a computer-readable medium having stored thereon computer-readable instructions for carrying out a method for identifying any CNV e.g. chromosomal or partial aneuploidies. In one embodiment, the invention provides a computer-readable medium having stored thereon computer-readable instructions for identifying a chromosome suspected to be involved with a chromosomal aneuploidy e.g. trisomy 21, trisomy, 13, trisomy 18, or monosomy X.

In one embodiment, the invention provides a computer-readable medium having stored thereon computer-readable instructions for carrying out a method for identifying fetal trisomy 21, said method comprising the steps: (a) obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. In one embodiment, the at least one normalizing chromosome is selected from the group of chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the at least one normalizing chromosome is selected from the group of chromosome 9, chromosome 1, chromosome 2, chromosome 11, chromosome 12, and chromosome 14. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis, sequencing-by-ligation, or pyrosequencing. Preferably, the sequencing method is massively parallel sequencing-by-synthesis using reversible dye terminators. In other embodiments, the sequencing method is Sanger sequencing. In some embodiments, the sequencing method comprises an amplification e.g. a PCR amplification. In some embodiments, the computer-readable medium having stored thereon computer-readable instructions for identifying fetal trisomy 21 carries out a method comprising the steps of (a) using sequence information obtained from a plurality of fetal and maternal nucleic acid molecules in a maternal plasma sample to identify a number of mapped sequence tags for chromosome 21; (b) using sequence information obtained from a plurality of fetal and maternal nucleic acid molecules in a maternal plasma sample to identify a number of mapped sequence tags for at least one normalizing chromosome; (c) using the number of mapped sequence tags identified for chromosome 21 in step (a) and the number of mapped sequence tags identified for the at least one normalizing chromosome in step (b) to calculate a chromosome dose for chromosome 21; and (d) comparing said chromosome dose to at least one threshold value, and thereby identifying the presence or absence of fetal trisomy 21.

In one embodiment, the invention provides a computer-readable medium having stored thereon computer-readable instructions for carrying out a method for identifying fetal trisomy 21 in a maternal plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. In one embodiment, the at least one normalizing chromosome is selected from the group chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the at least one normalizing chromosome is selected from the group of chromosome 9, chromosome 1, chromosome 2, chromosome 11, chromosome 12, and chromosome 14. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In one embodiment, the computer-readable medium having stored thereon computer-readable instructions for identifying fetal trisomy 21 carries out a method comprising the steps of (a) using sequence information obtained from a plurality of fetal and maternal nucleic acid molecules in a maternal plasma sample to identify a number of mapped sequence tags for chromosome 21; (b) using sequence information obtained from a plurality of fetal and maternal nucleic acid molecules in a maternal plasma sample to identify a number of mapped sequence tags for at least one normalizing chromosome; (c) using the number of mapped sequence tags identified for chromosome 21 in step (a) and the number of mapped sequence lags identified for the at least one normalizing chromosome in step (b) to calculate a chromosome dose for chromosome 21; and (d) comparing said chromosome dose to at least one threshold value, and thereby identifying the presence or absence of fetal trisomy 21. The computer-readable medium can be used for identifying other fetal trisomies e.g. trisomy 13, trisomy 18, trisomy 21, and chromosomal monosomies e.g. monosomy X.

In another embodiment, a computer-readable medium having stored thereon computer-readable instructions is provided for carrying out a method for identifying fetal trisomy 18 in a maternal plasma sample comprising fetal and maternal nucleic acid molecules, according to the method described for trisomy 21 wherein the normalizing chromosome for identifying trisomy 18 is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing chromosome for identifying trisomy 18 is selected from chromosome 8, chromosome 2, chromosome 3, chromosome 5, chromosome 6, chromosome 12, and chromosome 14.

In another embodiment, a computer-readable medium having stored thereon computer-readable instructions is provided for carrying out a method for identifying fetal trisomy 13 in a maternal plasma sample comprising fetal and maternal nucleic acid molecules, according to the method described for trisomy 21 wherein the normalizing chromosome for identifying trisomy 13 is selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. In some embodiments, the at least one normalizing chromosome is a group of chromosomes selected from chromosome 2, chromosome 3, chromosome 4, chromosome 5, chromosome 6, and chromosome 8. Preferably, the normalizing chromosome for identifying trisomy 13 is a group of chromosomes selected from chromosome 2, chromosome 3, chromosome 4, chromosome 5 and chromosome 6.

In another embodiment, a computer-readable medium having stored thereon computer-readable instructions is provided for carrying out a method for identifying fetal monosomy X in a maternal plasma sample comprising fetal and maternal nucleic acid molecules, according to the method described for monosomy X wherein the normalizing chromosome for identifying monosomy X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing chromosome is selected from chromosome 2, chromosome 3, chromosome 4, chromosome 5, chromosome 6, and chromosome 8. Alternatively, the normalizing chromosome is a group of chromosomes selected from chromosome 2, chromosome 3, chromosome 4, chromosome 5, chromosome 6, and chromosome 8. In one embodiment, the method for identifying fetal monosomy X further comprises determining the presence or absence of chromosome Y, comprising the steps: (a) using the sequence information to identify a number of mapped sequence tags for chromosome Y; (b) using the sequence information to identify a number of mapped sequence tags for at least one normalizing chromosome; (c) using the number of mapped sequence tags identified for chromosome Y in step (a) and the number of mapped sequence tags identified for the at least one normalizing chromosome in step (b) to calculate a chromosome dose for chromosome Y; and (d) comparing said chromosome dose to at least one threshold value, and thereby identifying the presence or absence of fetal chromosome Y. In one embodiment, obtaining the sequence information comprises sequencing at least a portion of said nucleic acid molecules, thereby obtaining sequence information for a plurality of fetal and maternal nucleic acid molecules of a maternal plasma sample. In one embodiment, step (c) comprises calculating a chromosome dose for chromosome Y as the ratio of the number of mapped sequence tags identified for chromosome Y and the number of mapped sequence tags identified for the at least one normalizing chromosome. Alternatively, step (c) comprises (i) calculating a sequence tag density ratio for chromosome Y, by relating the number of mapped sequence tags identified for chromosome Y in step (a) to the length of chromosome Y; (ii) calculating a sequence tag density ratio for said at least one normalizing chromosome, by relating the number of mapped sequence tags identified for said at least one normalizing chromosome in step (b) to the length of said at least one normalizing chromosome; and (iii) using the sequence tag density ratios calculated in steps (i) and (ii) to calculate a chromosome dose for chromosome Y, wherein the chromosome dose is calculated as the ratio of the sequence tag density ratio for chromosome Y and the sequence tag density ratio for said at least one normalizing chromosome. Any one chromosome, or a group of two or more chromosomes selected from chromosomes 1-22 and chromosome X can be used as the normalizing chromosome for chromosome Y. In one embodiment, the at least one normalizing chromosome is a group of chromosomes consisting of chromosomes 1-22, and chromosome X.

The method of the invention can be performed using a computer processing system which is adapted or configured to perform a method for identifying any CNV e.g. chromosomal or partial aneuploidies. In one embodiment, the invention provides a computer processing system which is adapted or configured to perform a method for identifying fetal trisomy 21, said method comprising the steps: (a) obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. In one embodiment, the at least one normalizing chromosome is selected from the group consisting of chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In one embodiment, a computer processing system that is adapted or configured for carrying out a method comprising the steps of: (a) using sequence information obtained from a plurality of fetal and maternal nucleic acid molecules in a maternal plasma sample to identify a number of mapped sequence tags for chromosome 21; (b) using sequence information obtained from a plurality of fetal and maternal nucleic acid molecules in a maternal plasma sample to identify a number of mapped sequence tags for at least one normalizing chromosome; (c) using the number of mapped sequence tags identified for chromosome 21 in step (a) and the number of mapped sequence tags identified for the at least one normalizing chromosome in step (b) to calculate a chromosome dose for chromosome 21; and (d) comparing said chromosome dose to at least one threshold value, and thereby identifying the presence or absence of fetal trisomy 21.

In one embodiment, the invention provides a computer processing system that is adapted or configured to perform a method for identifying fetal trisomy 21 in a maternal plasma sample comprising fetal and maternal nucleic acid molecules, and comprises the steps: (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. In one embodiment, the at least one normalizing chromosome is selected from the group consisting of chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In one embodiment, a computer processing system is adapted or configured for carrying out a method comprising the steps of: (a) using sequence information obtained from a plurality of fetal and maternal nucleic acid molecules in a maternal plasma sample to identify a number of mapped sequence tags for chromosome 21; (b) using sequence information obtained from a plurality of fetal and maternal nucleic acid molecules in a maternal plasma sample to identify a number of mapped sequence tags for at least one normalizing chromosome; (c) using the number of mapped sequence tags identified for chromosome 21 in step (a) and the number of mapped sequence tags identified for the at least one normalizing chromosome in step (b) to calculate a chromosome dose for chromosome 21; and (d) comparing said chromosome dose to at least one threshold value, and thereby identifying the presence or absence of fetal trisomy 21.

In another embodiment, the computer processing system is adapted or configured for identifying fetal trisomy 18 in a maternal plasma sample comprising fetal and maternal nucleic acid molecules, according to the method described for trisomy 21 wherein the normalizing chromosome for identifying trisomy 18 is selected from trisomy 18 wherein the normalizing chromosome for identifying trisomy 18 is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14.

In another embodiment, the computer processing system is adapted or configured for identifying fetal trisomy 13 in a maternal plasma sample comprising fetal and maternal nucleic acid molecules, according to the method described for trisomy 21 wherein the normalizing chromosome for identifying trisomy 13 is selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing chromosome for identifying trisomy 13 is a combination of a group of chromosomes consisting of chromosome 2, chromosome 3, chromosome 4, chromosome 5 and chromosome 6.

In another embodiment, the computer processing system is adapted or configured for identifying fetal monosomy X in a maternal plasma sample comprising fetal and maternal nucleic acid molecules, according to the method described for trisomy 21 wherein the normalizing chromosome for identifying monosomy X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. In one embodiment, the method for identifying fetal monosomy X further comprises determining the presence or absence of chromosome Y, comprising the steps: (a) using the sequence information to identify a number of mapped sequence tags for chromosome Y; (b) using the sequence information to identify a number of mapped sequence tags for at least one normalizing chromosome; (c) using the number of mapped sequence tags identified for chromosome Y in step (a) and the number of mapped sequence tags identified for the at least one normalizing chromosome in step (b) to calculate a chromosome dose for chromosome Y; and (d) comparing said chromosome dose to at least one threshold value, and thereby identifying the presence or absence of fetal chromosome Y. In one embodiment, obtaining the sequence information comprises sequencing at least a portion of said nucleic acid molecules, thereby obtaining sequence information for a plurality of fetal and maternal nucleic acid molecules of a maternal plasma sample. In one embodiment, step (c) comprises calculating a chromosome dose for chromosome Y as the ratio of the number of mapped sequence tags identified for chromosome Y and the number of mapped sequence tags identified for the at least one normalizing chromosome. Alternatively, step (c) comprises (i) calculating a sequence tag density ratio for chromosome Y, by relating the number of mapped sequence tags identified for chromosome Y in step (a) to the length of chromosome Y; (ii) calculating a sequence tag density ratio for said at least one normalizing chromosome, by relating the number of mapped sequence tags identified for said at least one normalizing chromosome in step (b) to the length of said at least one normalizing chromosome; and (iii) using the sequence tag density ratios calculated in steps (i) and (ii) to calculate a chromosome dose for chromosome Y, wherein the chromosome dose is calculated as the ratio of the sequence tag density ratio for chromosome Y and the sequence tag density ratio for said at least one normalizing chromosome. Any one chromosome, or a group of two or more chromosomes selected from chromosomes 1-22 and chromosome X can be used as the normalizing chromosome for chromosome Y. In one embodiment, the at least one normalizing chromosome is a group of chromosomes consisting of chromosomes 1-22, and chromosome X.

In one embodiment, the invention provides an apparatus that is adapted and configured to perform a method of identifying a CNV e.g. a chromosomal or a partial aneuploidy, as described herein. In one embodiment, the apparatus is configured to perform a method for identify fetal trisomy 21 comprising: (a) obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. In one embodiment, the at least one normalizing chromosome is selected from the group consisting of chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In one embodiment, the apparatus that is configured to identify fetal trisomy 21 comprises (a) a sequencing device adapted or configured for sequencing at least a portion of the nucleic acid molecules in a maternal plasma sample comprising fetal and maternal nucleic acid molecules, thereby generating sequence information; and (b) a computer processing system configured to perform the following steps: (i) using sequence information generated by the sequencing device to identify a number of mapped sequence tags for chromosome 21; (ii) using sequence information generated by the sequencing device to identify a number of mapped sequence tags for at least one normalizing chromosome; (iii) using the number of mapped sequence tags identified for chromosome 21 in step (i) and the number of mapped sequence tags identified for the at least one normalizing chromosome in step (ii) to calculate a chromosome dose for chromosome 21; and (iv) comparing said chromosome dose to at least one threshold value, and thereby identifying the presence or absence of fetal trisomy 21.

In one embodiment, an apparatus is provided that is adapted or configured to perform a method for identifying fetal trisomy 21 in a maternal plasma sample comprising fetal and maternal nucleic acid molecules, which method comprises (a) sequencing at least a portion of said nucleic acid molecules, thereby obtaining sequence information for a plurality of fetal and maternal nucleic acid molecules of a maternal plasma sample; (b) using the sequence information to identify a number of mapped sequence tags for chromosome 21; (c) using the sequence information to identify a number of mapped sequence tags for at least one normalizing chromosome; (d) using the number of mapped sequence tags identified for chromosome 21 in step (b) and the number of mapped sequence tags identified for the at least one normalizing chromosome in step (c) to calculate a chromosome dose for chromosome 21; and (e) comparing said chromosome dose to at least one threshold value, and thereby identifying the presence or absence of fetal trisomy 21. In one embodiment, step (d) comprises calculating a chromosome dose for chromosome 21 as the ratio of the number of mapped sequence tags identified for chromosome 21 and the number of mapped sequence tags identified for the at least one normalizing chromosome. Alternatively, step (d) comprises (i) calculating a sequence tag density ratio for chromosome 21, by relating the number of mapped sequence tags identified for chromosome 21 in step (b) to the length of chromosome 21; (ii) calculating a sequence tag density ratio for said at least one normalizing chromosome, by relating the number of mapped sequence tags identified for said at least one normalizing chromosome in step (c) to the length of said at least one normalizing chromosome; and (iii) using the sequence tag density ratios calculated in steps (i) and (ii) to calculate a chromosome dose for chromosome 21, wherein the chromosome dose is calculated as the ratio of the sequence tag density ratio for chromosome 21 and the sequence tag density ratio for said at least one normalizing chromosome. The at least one normalizing chromosome is selected form the group of chromosome 9, chromosome 1, chromosome 10, chromosome 11 and chromosome 15. In one embodiment, the fetal and maternal nucleic acid molecules are cell-free DNA molecules. In some embodiments, the sequencing method for identifying the fetal trisomy 21 is a next generation sequencing method. In some embodiments, the sequencing method is a massively parallel sequencing method that uses sequencing-by-synthesis with reversible dye terminators. In other embodiments, the sequencing method is sequencing-by-ligation. In some embodiments, sequencing comprises an amplification. In some embodiments, sequencing comprises PCR amplification. In one embodiment, the apparatus, which is adapted or configured for identifying fetal trisomy 21 in a maternal plasma sample comprising fetal and maternal nucleic acid molecules, comprises: (a) a sequencing device adapted or configured for sequencing at least a portion of the nucleic acid molecules in a maternal plasma sample comprising fetal and maternal nucleic acid molecules, thereby generating sequence information; and (b) a computer processing system configured to perform the following steps: (i) using sequence information generated by the sequencing device to identify a number of mapped sequence tags for chromosome 21; (ii) using sequence information generated by the sequencing device to identify a number of mapped sequence tags for at least one normalizing chromosome; (iii) using the number of mapped sequence tags identified for chromosome 21 in step (i) and the number of mapped sequence tags identified for the at least one normalizing chromosome in step (ii) to calculate a chromosome dose for chromosome 21; and (iv) comparing said chromosome dose to at least one threshold value, and thereby identifying the presence or absence of fetal trisomy 21.

In another embodiment, the apparatus is adapted or configured for identifying fetal trisomy 18 in a maternal plasma sample comprising fetal and maternal nucleic acid molecules, according to the method described for trisomy 21 wherein the normalizing chromosome for identifying trisomy 18 is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14.

In another embodiment, the apparatus is adapted or configured for identifying fetal trisomy 13 in a maternal plasma sample comprising fetal and maternal nucleic acid molecules, according to the method described for trisomy 21 wherein the normalizing chromosome for identifying trisomy 13 is selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing chromosome for identifying trisomy 13 is a combination of a group of chromosomes consisting of chromosome 2, chromosome 3, chromosome 4, chromosome 5 and chromosome 6.

In another embodiment, the apparatus is adapted or configured for identifying fetal monosomy X in a maternal plasma sample comprising fetal and maternal nucleic acid molecules, according to the method described for identifying trisomy 21 wherein the normalizing chromosome for identifying monosomy X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. In one embodiment, the method for identifying fetal monosomy X further comprises determining the presence or absence of chromosome Y, comprising the steps: (a) using the sequence information to identify a number of mapped sequence tags for chromosome Y; (b) using the sequence information to identify a number of mapped sequence tags for at least one normalizing chromosome; (c) using the number of mapped sequence tags identified for chromosome Y in step (a) and the number of mapped sequence tags identified for the at least one normalizing chromosome in step (b) to calculate a chromosome dose for chromosome Y; and (d) comparing said chromosome dose to at least one threshold value, and thereby identifying the presence or absence of fetal chromosome Y. In one embodiment, obtaining the sequence information comprises sequencing at least a portion of said nucleic acid molecules, thereby obtaining sequence information for a plurality of fetal and maternal nucleic acid molecules of a maternal plasma sample. In one embodiment, step (c) comprises calculating a chromosome dose for chromosome Y as the ratio of the number of mapped sequence tags identified for chromosome Y and the number of mapped sequence tags identified for the at least one normalizing chromosome.

Alternatively, step (c) comprises (i) calculating a sequence tag density ratio for chromosome Y, by relating the number of mapped sequence tags identified for chromosome Y in step (a) to the length of chromosome Y; (ii) calculating a sequence tag density ratio for said at least one normalizing chromosome, by relating the number of mapped sequence tags identified for said at least one normalizing chromosome in step (b) to the length of said at least one normalizing chromosome; and (iii) using the sequence tag density ratios calculated in steps (i) and (ii) to calculate a chromosome dose for chromosome Y, wherein the chromosome dose is calculated as the ratio of the sequence tag density ratio for chromosome Y and the sequence tag density ratio for said at least one normalizing chromosome. Any one chromosome, or a group of two or more chromosomes selected from chromosomes 1-22 and chromosome X can be used as the normalizing chromosome for chromosome Y. In one embodiment, the at least one normalizing chromosome is a group of chromosomes consisting of chromosomes 1-22, and chromosome X.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

7. EXPERIMENTAL

Example 1

Sample Processing and DNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma was stored at −80° C. and thawed only once before DNA extraction.

Cell-free DNA was extracted from cell-free plasma by using QIAamp DNA Blood Mini kit (Qiagen) according to the manufacturer's instructions. Five milliliters of buffer AL and 500 µl of Qiagen Protease were added to 4.5 ml-5 ml of cell-free plasma. The volume was adjusted to 10 ml with phosphate buffered saline (PBS), and the mixture was incubated at 56° C. for 12 minutes. Multiple columns were used to separate the precipitated cfDNA from the solution by centrifugation at 8,000 RPM in a Beckman microcentrifuge. The columns were washed with AW1 and AW2 buffers, and the cfDNA was eluted with 55 µl of nuclease-free water. Approximately 3.5-7 ng of cfDNA was extracted from the plasma samples.

All sequencing libraries were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5° exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Mellow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PM purification system (Part No, A63881; Beckman Coulter Genomics, Danvers, Mass.). Eighteen cycles of PCR were performed to selectively enrich adaptor-ligated cfDNA using Phusion® High-Fidelity Master Mix (Finnzymes, Woburn, Mass.) and Illumina's PCR primers complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30 seconds; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available on the worldwide web at beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome. Upon completion of sequencing of the sample, the Illumina "Sequencer Control Software" transferred image and base call files to a Unix server running the Illumina "Genome Analyzer Pipeline" software version 1.51. The Illumina "Gerald" program was run to align sequences to the reference human genome that is derived from the hg18 genome provided by National Center for Biotechnology Information (NCBI36/hg18, available on the world wide web at genome.ucsc.edu/cgi-bin/hgGateway?org=Human&db=hg18&hgsid=166260105). The sequence data generated from the above procedure that uniquely aligned to the genome was read from Gerald output (export.txt files) by a program (c2c.pl) running on a computer running the Linux operating system. Sequence alignments with base mis-matches were allowed and included in alignment counts only if they aligned uniquely to the genome. Sequence alignments with identical start and end coordinates (duplicates) were excluded.

Between about 5 and 15 million 36 bp tags with 2 or less mismatches were mapped uniquely to the human genome. All mapped tags were counted and included in the calculation of chromosome doses in both test and qualifying samples. Regions extending from base 0 to base $2\times10^6$, base $10\times10^6$ to base $13\times10^6$, and base $23\times10^6$ to the end of chromosome Y, were specifically excluded from the analysis because tags derived from either male or female fetuses map to these regions of the Y-chromosome.

It was noted that some variation in the total number of sequence tags mapped to individual chromosomes across samples sequenced in the same run (inter-chromosomal variation), but substantially greater variation was noted to occur among different sequencing runs (inter-sequencing run variation).

Example 2

Dose and Variance for Chromosomes 13, 18, 21, X, and Y

To examine the extent of inter-chromosomal and inter-sequencing variation in the number of mapped sequence tags for all chromosomes, plasma cfDNA obtained from peripheral blood of 48 volunteer pregnant subjects was extracted and sequenced as described in Example 1, and analyzed as follows.

The total number of sequence tags that were mapped to each chromosome (sequence tag density) was determined. Alternatively, the number of mapped sequence tags may be normalized to the length of the chromosome to generate a sequence tag density ratio. The normalization to chromosome length is not a required step, and can be performed solely to reduce the number of digits in a number to simplify it for human interpretation. Chromosome lengths that can be used to normalize the sequence tags counts can be the lengths provided on the world wide web at genome.ucsc.edu/goldenPath/stats.html#hg18.

Figure 7:
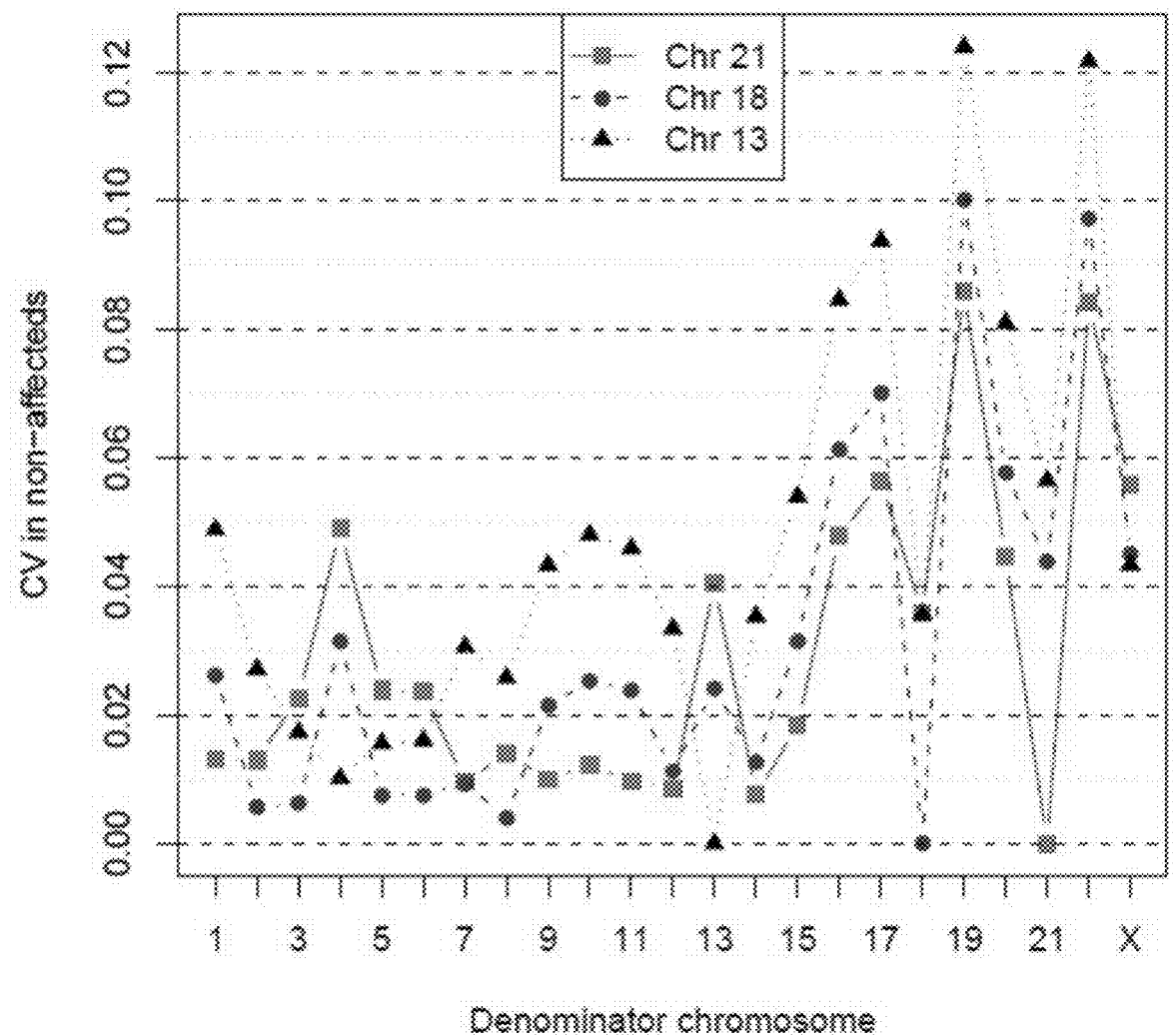
Figure 8:
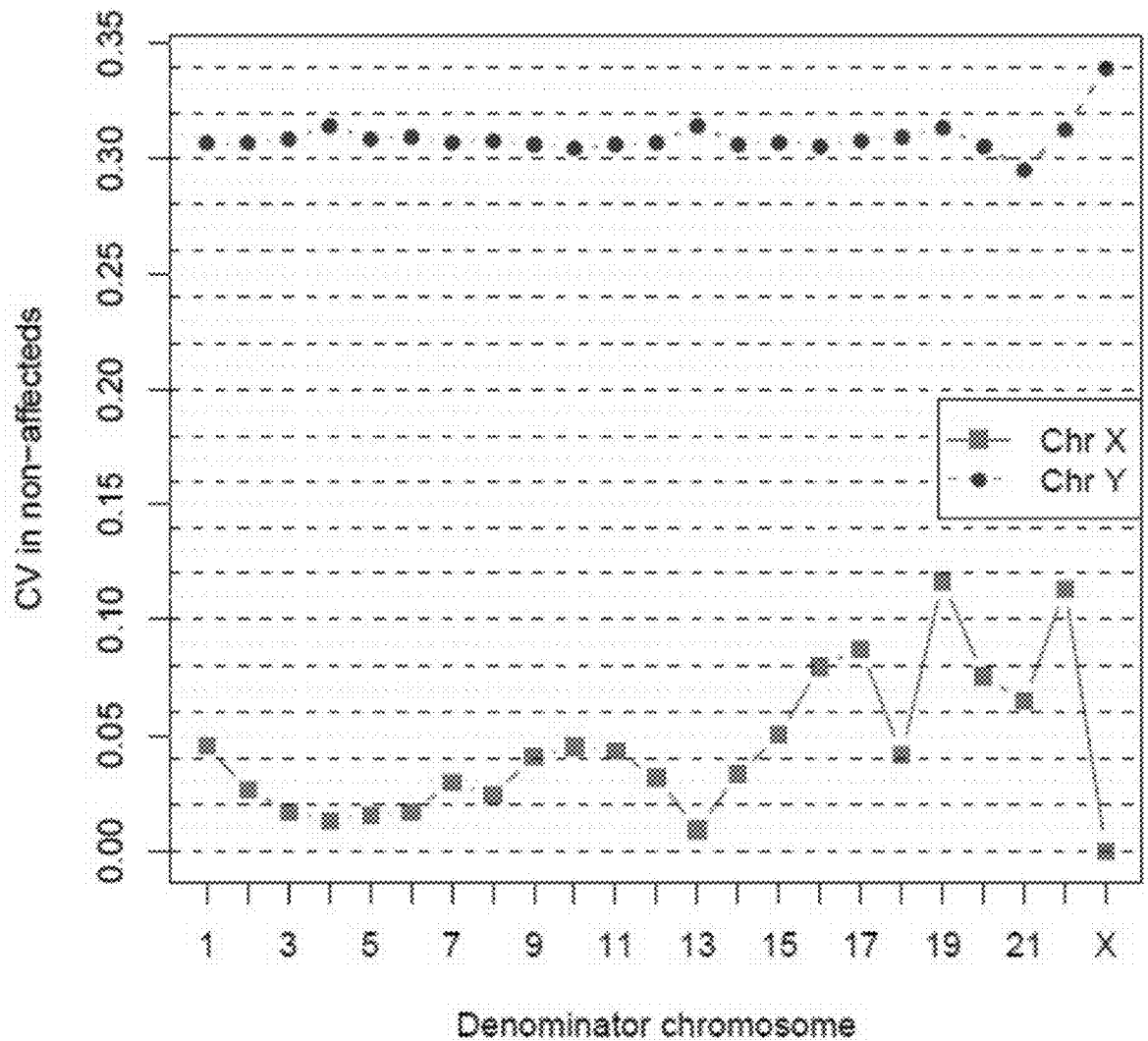
FIG. 8 shows the coefficient of variation (CV) for chromosomes X (■) and Y (●) that was determined from the doses shown in FIGS. 5 and 6, respectively.
Figure 9:
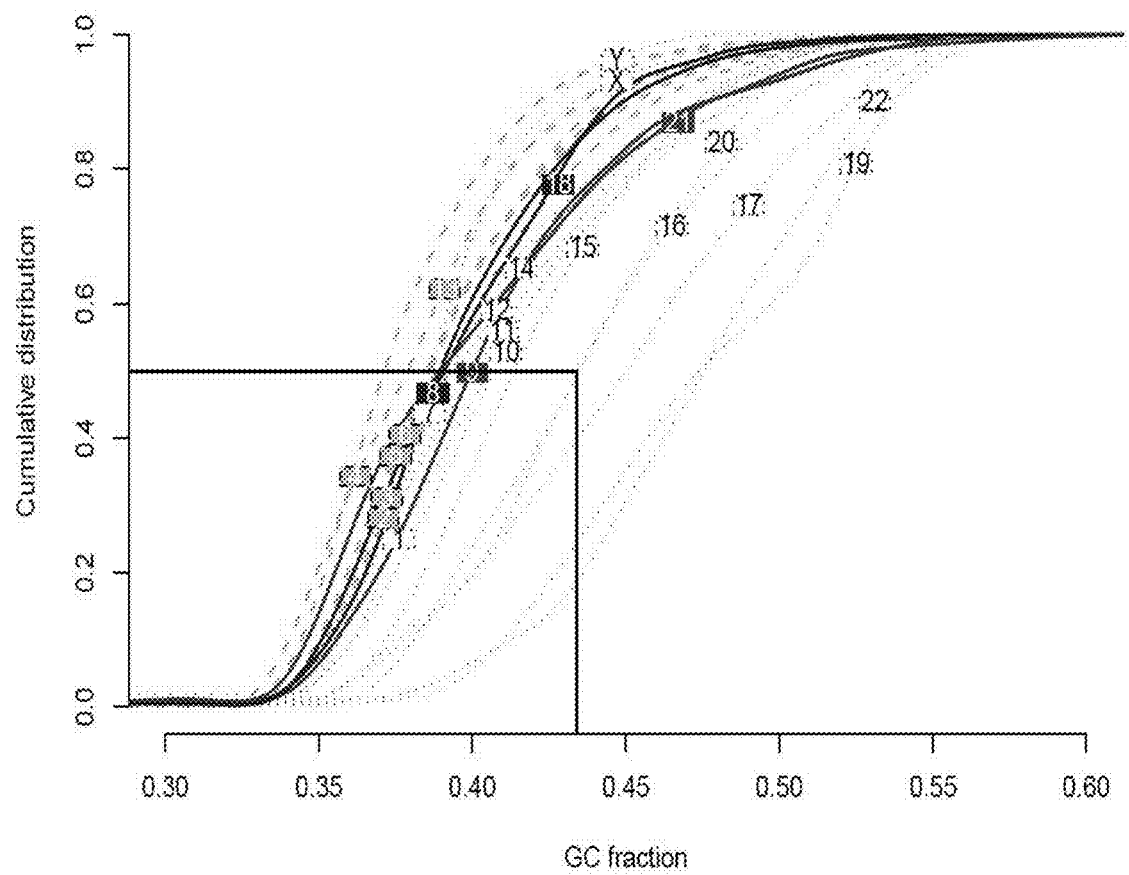
FIG. 9 shows the cumulative distribution of GC fraction by human chromosome. The vertical axis represents the frequency of the chromosome with GC content below the value shown on the horizontal axis.

The resulting sequence tag density for each chromosome was related to the sequence tag density of each of the remaining chromosomes to derive a qualified chromosome dose, which was calculated as the ratio of the sequence tag density for the chromosome of interest e.g. chromosome 21, and the sequence tag density of each of the remaining chromosomes i.e. chromosomes 1-20, 22 and X. Table 1 provides an example of the calculated qualified chromosome dose for chromosomes of interest 13, 18, 21, X, and Y, determined in one of the qualified samples. Chromosomes doses were determined for all chromosomes in all samples, and the average doses for chromosomes of interest 13, 18, 21, X and Y in the qualified samples are provided in Tables 2 and 3, and depicted in FIGS. 2A-6B. FIGS. 2A-6B also depict the chromosome doses for the test samples. The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome, that has a variation among samples that is closest to the variation of the chromosome of interest, and that would serve as ideal sequences for normalizing values for further statistical evaluation. FIGS. 7 and 8 depict the calculated average chromosome doses determined in a population of qualified samples for chromosomes 13, 18, and 21, and chromosomes X and Y.

In some instances, the best normalizing chromosome may not have the least variation, but may have a distribution of qualified doses that best distinguishes a test sample or samples from the qualified samples i.e. the best normalizing chromosome may not have the lowest variation, but may have the greatest differentiability. Thus, differentiability accounts for the variation in chromosome dose and the distribution of the doses in the qualified samples.

Tables 2 and 3 provide the coefficient of variation as the measure of variability, and student t-test values as a measure of differentiability for chromosomes 18, 21, X and Y, wherein the smaller the T-test value, the greatest the differentiability. The differentiability for chromosome 13 was determined as the ratio of difference between the mean chromosome dose in the qualified samples and the dose for chromosome 13 in the only T13 test sample, and the standard deviation of mean of the qualified dose.

The qualified chromosome doses also serve as the basis for determining threshold values when identifying aneuploidies in test samples as described in the following.

TABLE 1

Qualified Chromosome Dose for Chromosomes 13, 18, 21, X and Y (n = 1; sample #11342, 46 XY)

| Chromosome | chr 21 | chr 18 | chr 13 | chr X | chr Y |
|---|---|---|---|---|---|
| chr1 | 0.149901 | 0.306798 | 0.341832 | 0.490969 | 0.003958 |
| chr2 | 0.15413 | 0.315452 | 0.351475 | 0.504819 | 0.004069 |
| chr3 | 0.193331 | 0.395685 | 0.44087 | 0.633214 | 0.005104 |
| chr4 | 0.233056 | 0.476988 | 0.531457 | 0.763324 | 0.006153 |
| chr5 | 0.219209 | 0.448649 | 0.499882 | 0.717973 | 0.005787 |
| chr6 | 0.228548 | 0.467763 | 0.521179 | 0.748561 | 0.006034 |
| chr7 | 0.245124 | 0.501688 | 0.558978 | 0.802851 | 0.006472 |
| chr8 | 0.256279 | 0.524519 | 0.584416 | 0.839388 | 0.006766 |
| chr9 | 0.309871 | 0.634203 | 0.706625 | 1.014915 | 0.008181 |
| chr10 | 0.25122 | 0.514164 | 0.572879 | 0.822817 | 0.006633 |
| chr11 | 0.257168 | 0.526338 | 0.586443 | 0.8423 | 0.00679 |
| chr12 | 0.275192 | 0.563227 | 0.627544 | 0.901332 | 0.007265 |
| chr13 | 0.438522 | 0.897509 | 1 | 1.436285 | 0.011578 |
| chr14 | 0.405957 | 0.830858 | 0.925738 | 1.329624 | 0.010718 |
| chr15 | 0.406855 | 0.832697 | 0.927786 | 1.332566 | 0.010742 |
| chr16 | 0.376148 | 0.769849 | 0.857762 | 1.231991 | 0.009931 |
| chr17 | 0.383027 | 0.783928 | 0.873448 | 1.254521 | 0.010112 |
| chr18 | 0.488599 | 1 | 1.114194 | 1.600301 | 0.0129 |
| chr19 | 0.535867 | 1.096742 | 1.221984 | 1.755118 | 0.014148 |
| chr20 | 0.467308 | 0.956424 | 1.065642 | 1.530566 | 0.012338 |
| chr21 | 1 | 2.046668 | 2.280386 | 3.275285 | 0.026401 |
| chr22 | 0.756263 | 1.547819 | 1.724572 | 2.476977 | 0.019966 |
| chrX | 0.305317 | 0.624882 | 0.696241 | 1 | 0.008061 |
| chrY | 37.87675 | 77.52114 | 86.37362 | 124.0572 | 1 |

TABLE 2

Qualified Chromosome Dose, Variance and Differentiability for chromosomes 21, 18 and 13

| | 21 (n = 35) | | | | 18 (n = 40) | | | |
|---|---|---|---|---|---|---|---|---|
| | Avg | Stdev | CV | T Test | Avg | Stdev | CV | T Test |
| chr1 | 0.15335 | 0.001997 | 1.30 | 3.18E−10 | 0.31941 | 0.008384 | 2.62 | 0.001675 |
| chr2 | 0.15267 | 0.001966 | 1.29 | 9.87E−07 | 0.31807 | 0.001756 | 0.55 | 4.39E−05 |
| chr3 | 0.18936 | 0.004233 | 2.24 | 1.04E−05 | 0.39475 | 0.002406 | 0.61 | 3.39E−05 |
| chr4 | 0.21998 | 0.010668 | 4.85 | 0.000501 | 0.45873 | 0.014292 | 3.12 | 0.001349 |
| chr5 | 0.21383 | 0.005058 | 2.37 | 1.43E−05 | 0.44582 | 0.003288 | 0.74 | 3.09E−05 |
| chr6 | 0.22435 | 0.005258 | 2.34 | 1.48E−05 | 0.46761 | 0.003481 | 0.74 | 2.32E−05 |
| chr7 | 0.24348 | 0.002298 | 0.94 | 2.05E−07 | 0.50765 | 0.004669 | 0.92 | 9.07E−05 |
| chr8 | 0.25269 | 0.003497 | 1.38 | 1.52E−06 | 0.52677 | 0.002046 | 0.39 | 4.89E−05 |
| chr9 | 0.31276 | 0.003095 | 0.99 | 3.83E−09 | 0.65165 | 0.013851 | 2.13 | 0.000559 |
| chr10 | 0.25618 | 0.003112 | 1.21 | 2.28E−10 | 0.53354 | 0.013431 | 2.52 | 0.002137 |
| chr11 | 0.26075 | 0.00247 | 0.95 | 1.08E−09 | 0.54324 | 0.012859 | 2.37 | 0.000998 |
| chr12 | 0.27563 | 0.002316 | 0.84 | 2.04E−07 | 0.57445 | 0.006495 | 1.13 | 0.000125 |
| chr13 | 0.41828 | 0.016782 | 4.01 | 0.000123 | 0.87245 | 0.020942 | 2.40 | 0.000164 |
| chr14 | 0.40671 | 0.002994 | 0.74 | 7.33E−08 | 0.84731 | 0.010864 | 1.28 | 0.000149 |
| chr15 | 0.41861 | 0.007686 | 1.84 | 1.85E−10 | 0.87164 | 0.027373 | 3.14 | 0.003862 |
| chr16 | 0.39977 | 0.018882 | 4.72 | 7.33E−06 | 0.83313 | 0.050781 | 6.10 | 0.075458 |
| chr17 | 0.41394 | 0.02313 | 5.59 | 0.000248 | 0.86165 | 0.060048 | 6.97 | 0.088579 |
| chr18 | 0.47236 | 0.016627 | 3.52 | 1.3E−07 | | | | |
| chr19 | 0.59435 | 0.05064 | 8.52 | 0.01494 | 1.23932 | 0.12315 | 9.94 | 0.231139 |
| chr20 | 0.49464 | 0.021839 | 4.42 | 2.16E−06 | 1.03023 | 0.058995 | 5.73 | 0.061101 |
| chr21 | | | | | 2.03419 | 0.08841 | 4.35 | 2.81E−05 |
| chr22 | 0.84824 | 0.070613 | 8.32 | 0.02209 | 1.76258 | 0.169864 | 9.64 | 0.181808 |
| chrX | 0.27846 | 0.015546 | 5.58 | 0.000213 | 0.58691 | 0.026637 | 4.54 | 0.064883 |

TABLE 3

Qualified Chromosome Dose, Variance and Differentiability for chromosomes 13, X, and Y

| | 13 (n = 47) | | | | X (n = 19) | | | |
|---|---|---|---|---|---|---|---|---|
| | Avg | Stdev | CV | Diff | Avg | Stdev | CV | T Test |
| chr1 | 0.36536 | 0.01775 | 4.86 | 1.904 | 0.56717 | 0.025988 | 4.58 | 0.001013 |
| chr2 | 0.36400 | 0.009817 | 2.70 | 2.704 | 0.56753 | 0.014871 | 2.62 | 9.6E−08 |
| chr3 | 0.45168 | 0.007809 | 1.73 | 3.592 | 0.70524 | 0.011932 | 1.69 | 6.13E−11 |
| chr4 | 0.52541 | 0.005264 | 1.00 | 3.083 | 0.82491 | 0.010537 | 1.28 | 1.75E−15 |
| chr5 | 0.51010 | 0.007922 | 1.55 | 3.944 | 0.79690 | 0.012227 | 1.53 | 1.29E−11 |
| chr6 | 0.53516 | 0.008575 | 1.60 | 3.758 | 0.83594 | 0.013719 | 1.64 | 2.79E−11 |
| chr7 | 0.58081 | 0.017692 | 3.05 | 2.445 | 0.90507 | 0.026437 | 2.92 | 7.41E−07 |
| chr8 | 0.60261 | 0.015434 | 2.56 | 2.917 | 0.93990 | 0.022506 | 2.39 | 2.11E−08 |
| chr9 | 0.74559 | 0.032065 | 4.30 | 2.102 | 1.15822 | 0.047092 | 4.07 | 0.000228 |
| chr10 | 0.61018 | 0.029139 | 4.78 | 2.060 | 0.94713 | 0.042866 | 4.53 | 0.000964 |
| chr11 | 0.62133 | 0.028323 | 4.56 | 2.081 | 0.96544 | 0.041782 | 4.33 | 0.000419 |
| chr12 | 0.65712 | 0.021853 | 3.33 | 2.380 | 1.02296 | 0.032276 | 3.16 | 3.95E−06 |
| chr13 | | | | | 1.56771 | 0.014258 | 0.91 | 2.47E−15 |
| chr14 | 0.96966 | 0.034017 | 3.51 | 2.233 | 1.50951 | 0.05009 | 3.32 | 8.24E−06 |
| chr15 | 0.99673 | 0.053512 | 5.37 | 1.888 | 1.54618 | 0.077547 | 5.02 | 0.002925 |
| chr16 | 0.95169 | 0.080007 | 8.41 | 1.613 | 1.46673 | 0.117073 | 7.98 | 0.114232 |
| chr17 | 0.98547 | 0.091918 | 9.33 | 1.484 | 1.51571 | 0.132775 | 8.76 | 0.188271 |
| chr18 | 1.13124 | 0.040032 | 3.54 | 2.312 | 1.74146 | 0.072447 | 4.16 | 0.001674 |
| chr19 | 1.41624 | 0.174476 | 12.32 | 1.306 | 2.16586 | 0.252888 | 11.68 | 0.460752 |
| chr20 | 1.17705 | 0.094807 | 8.05 | 1.695 | 1.81576 | 0.137494 | 7.57 | 0.08801 |
| chr21 | 2.33660 | 0.131317 | 5.62 | 1.927 | 3.63243 | 0.235392 | 6.48 | 0.00675 |
| chr22 | 2.01678 | 0.243883 | 12.09 | 1.364 | 3.08943 | 0.34981 | 11.32 | 0.409449 |
| chrX | 0.66679 | 0.028788 | 4.32 | 1.114 | | | | |
| chr2-6 | 0.46751 | 0.006762 | 1.45 | 4.066 | | | | |
| chr3-6 | 0.50332 | 0.005161 | 1.03 | 5.260 | | | | |
| chr_tot | | | | | 1.13209 | 0.038485 | 3.40 | 2.7E−05 |

TABLE 3-continued

Qualified Chromosome Dose, Variance and Differentiability for chromosomes 13, X, and Y

| | Y (n = 16) | | | |
|---|---|---|---|---|
| | Avg | Stdev | CV | T Test |
| Chr 1-22, X | 0.00734 | 0.002611 | 30.81 | 1.8E−12 |

Examples of diagnoses of T21, T13, T18 and a case of Turner syndrome obtained using the normalizing chromosomes, chromosome doses and differentiability for each of the chromosomes of interest are described in Example 3.

Example 3

Diagnosis of Fetal Aneuploidy Using Normalizing Chromosomes

To apply the use of chromosome doses for assessing aneuploidy in a biological test sample, maternal blood test samples were obtained from pregnant volunteers and cfDNA was prepared, sequenced and analyzed as described in Examples 1 and 2.

Trisomy 21

Table 4 provides the calculated dose for chromosome 21 in an exemplary test sample (#11403). The calculated threshold for the positive diagnosis of T21 aneuploidy was set at >2 standard deviations from the mean of the qualified (normal) samples. A diagnosis for T21 was given based on the chromosome dose in the test sample being greater than the set threshold. Chromosomes 14 and 15 were used as normalizing chromosomes in separate calculations to show that either a chromosome having the lowest variability e.g. chromosome 14, or a chromosome having the greatest differentiability e.g. chromosome 15, can be used to identify the aneuploidy. Thirteen T21 samples were identified using the calculated chromosome doses, and the aneuploidy samples were confirmed to be T21 by karyotype.

TABLE 4

Chromosome Dose for a T21 aneuploidy (sample #11403, 47 XY + 21)

| Chromosome | Sequence Tag Density | Chromosome Dose for Chr 21 | Threshold |
|---|---|---|---|
| Chr21 | 333,660 | 0.419672 | 0.412696 |
| Chr14 | 795,050 | | |
| Chr21 | 333,660 | 0.441038 | 0.433978 |
| Chr15 | 756,533 | | |

Trisomy 18

Table 5 provides the calculated dose for chromosome 18 in a test sample (#11390). The calculated threshold for the positive diagnosis of T18 aneuploidy was set at 2 standard deviations from the mean of the qualified (normal) samples. A diagnosis for T18 was given based on the chromosome dose in the test sample being greater than the set threshold. Chromosome 8 was used as the normalizing chromosome. In this instance chromosome 8 had the lowest variability and the greatest differentiability. Eight T18 samples were identified using chromosome doses, and were confirmed to be T18 by karyotype.

These data show that a normalizing chromosome can have both the lowest variability and the greatest differentiability.

TABLE 5

Chromosome Dose for a T18 aneuploidy (sample #11390, 47 XY + 18)

| Chromosome | Sequence Tag Density | Chromosome Dose for Chr 18 | Threshold |
|---|---|---|---|
| Chr18 | 602,506 | 0.585069 | 0.530867 |
| Chr8 | 1,029,803 | | |

Trisomy 13

Table 6 provides the calculated dose for chromosome 13 in a test sample (#51236). The calculated threshold for the positive diagnosis of T13 aneuploidy was set at 2 standard deviations from the mean of the qualified samples. A diagnosis for T13 was given based on the chromosome dose in the test sample being greater than the set threshold. The chromosome dose for chromosome 13 was calculated using either chromosome 5 or the group of chromosomes 3, 4, 5, and 6 as the normalizing chromosome. One T13 sample was identified.

TABLE 6

Chromosome Dose for a T13 aneuploidy (sample #51236, 47 XY + 13)

| Chromosome | Sequence Tag Density | Chromosome Dose for Chr 13 | Threshold |
|---|---|---|---|
| Chr13 | 692,242 | 0.541343 | 0.52594 |
| Chr5 | 1,278,749 | | |
| Chr13 | 692,242 | 0.530472 | 0.513647 |
| Chr3-6 [average] | 1,304,954 | | |

The sequence tag density for chromosomes 3-6 is the average tag counts for chromosomes 3-6.

The data show that the combination of chromosomes 3, 4, 5 and 6 provide a variability that is lower than that of chromosome 5, and the greatest differentiability than any of the other chromosomes.

Thus, a group of chromosomes can be used as the normalizing chromosome to determine chromosome doses and identify aneuploidies.

Turner Syndrome (Monosomy X)

Table 7 provides the calculated dose for chromosomes X and Y in a test sample (#51238). The calculated threshold for the positive diagnosis of Turner Syndrome (monosomy X) was set for the X chromosome at <−2 standard deviations from the mean, and for the absence of the Y chromosome at <−2 standard deviations from the mean for qualified (normal) samples.

TABLE 7

Chromosome Dose for a Turners (XO) aneuploidy (sample #51238, 45 X)

| Chromosome | Sequence Tag Density | Chromosome Dose for Chr X and Chr Y | Threshold |
|---|---|---|---|
| ChrX | 873,631 | 0.786642 | 0.803832 |
| Chr4 | 1,110,582 | | |
| ChrY | 1,321 | 0.001542101 | 0.00211208 |
| Chr_Total (1-22, X) (Average) | 856,623.6 | | |

A sample having an X chromosome dose less than that of the set threshold was identified as having less than one X chromosome. The same sample was determined to have a Y chromosome dose that was less than the set threshold, indicating that the sample did not have a Y chromosome. Thus, the combination of chromosome doses for X and Y were used to identify the Turner Syndrome (monosomy X) samples.

Thus, the method provided enables for the determination of CNV of chromosomes. In particular, the method enables for the determination of over- and under-representation chromosomal aneuploidies by massively parallel sequencing of maternal plasma cfDNA and identification of normalizing chromosomes for the statistical analysis of the sequencing data. The sensitivity and reliability of the method allow for accurate first and second trimester aneuploidy testing.

Example 4

Determination of Partial Aneuploidy

The use of sequence doses was applied for assessing partial aneuploidy in a biological test sample of cfDNA that was prepared from blood plasma, and sequenced as described in Example 1. The sample was confirmed by karyotyping to have been derived from a subject with a partial deletion of chromosome 11.

Analysis of the sequencing data for the partial aneuploidy (partial deletion of chromosome 11 i.e. q21-q23) was performed as described for the chromosomal aneuploidies in the previous examples. Mapping of the sequence tags to chromosome 11 in a test sample revealed a noticeable loss of tag counts between base pairs 81000082-103000103 in the q arm of the chromosome relative to the tag counts obtained for corresponding sequence on chromosome 11 in the qualified samples (data not shown). Sequence tags mapped to the sequence of interest on chromosome 11 (810000082-103000103 bp) in each of the qualified samples, and sequence tags mapped to all 20 megabase segments in the entire genome in the qualified samples i.e. qualified sequence tag densities, were used to determine qualified sequence doses as ratios of tag densities in all qualified samples. The average sequence dose, standard deviation, and coefficient of variation were calculated for all 20 megabase segments in the entire genome, and the 20-megabase sequence having the least variability was the identified normalizing sequence on chromosome 5 (13000014-33000033 bp) (See Table 8), which was used to calculate the dose for the sequence of interest in the test sample (see Table 9). Table 8 provides the sequence dose for the sequence of interest on chromosome 11 (810000082-103000103 bp) in the test sample that was calculated as the ratio of sequence tags mapped to the sequence of interest and the sequence tags mapped to the identified normalizing sequence. FIG. 10 shows the sequence doses for the sequence of interest in the 7 qualified samples (O) and the sequence dose for the corresponding sequence in the test sample (◇). The mean is shown by the solid line, and the calculated threshold for the positive diagnosis of partial aneuploidy that was set 5 standard deviations from the mean is shown by the dashed line. A diagnosis for partial aneuploidy was based on the sequence dose in the test sample being less than the set threshold. The test sample was verified by karyotyping to have deletion q21-q23 on chromosome 11.

Therefore, in addition to identifying chromosomal aneuploidies, the method of the invention can be used to identify partial aneuploidies.

TABLE 8

Qualified Normalizing Sequence, Dose and Variance for Sequence Chr11: 81000082-103000103 (qualified samples n = 7)

| | Chr11: 81000082-103000103 | | |
|---|---|---|---|
| | Avg | Stdev | CV |
| Chr5: 13000014-33000033 | 1.164702 | 0.004914 | 0.42 |

TABLE 9

Sequence Dose for Sequence of Interest (81000082-103000103) on Chromosome 11 (test sample 11206)

| Chromosome Segment | Sequence Tag Density | Chromosome Segment Dose for Chr 11 (q21-q23) | Threshold |
|---|---|---|---|
| Chr11: 81000082-103000103 | 27,052 | 1.0434313 | 1.1401347 |
| Chr5: 13000014-33000033 | 25,926 | | |

Example 5

Demonstration of Detection of Aneuploidy

Sequencing data obtained for the samples described in Examples 2 and 3, and shown in FIGS. 2A-6B were further analyzed to illustrate the sensitivity of the method in successfully identifying aneuploidies in maternal samples. Normalized chromosome doses for chromosomes 21, 18, 13 X and Y were analyzed as a distribution relative to the standard deviation of the mean (Y-axis) and shown in FIGS. 11A-11E. The normalizing chromosome used is shown as the denominator (X-axis).

Figure 11:
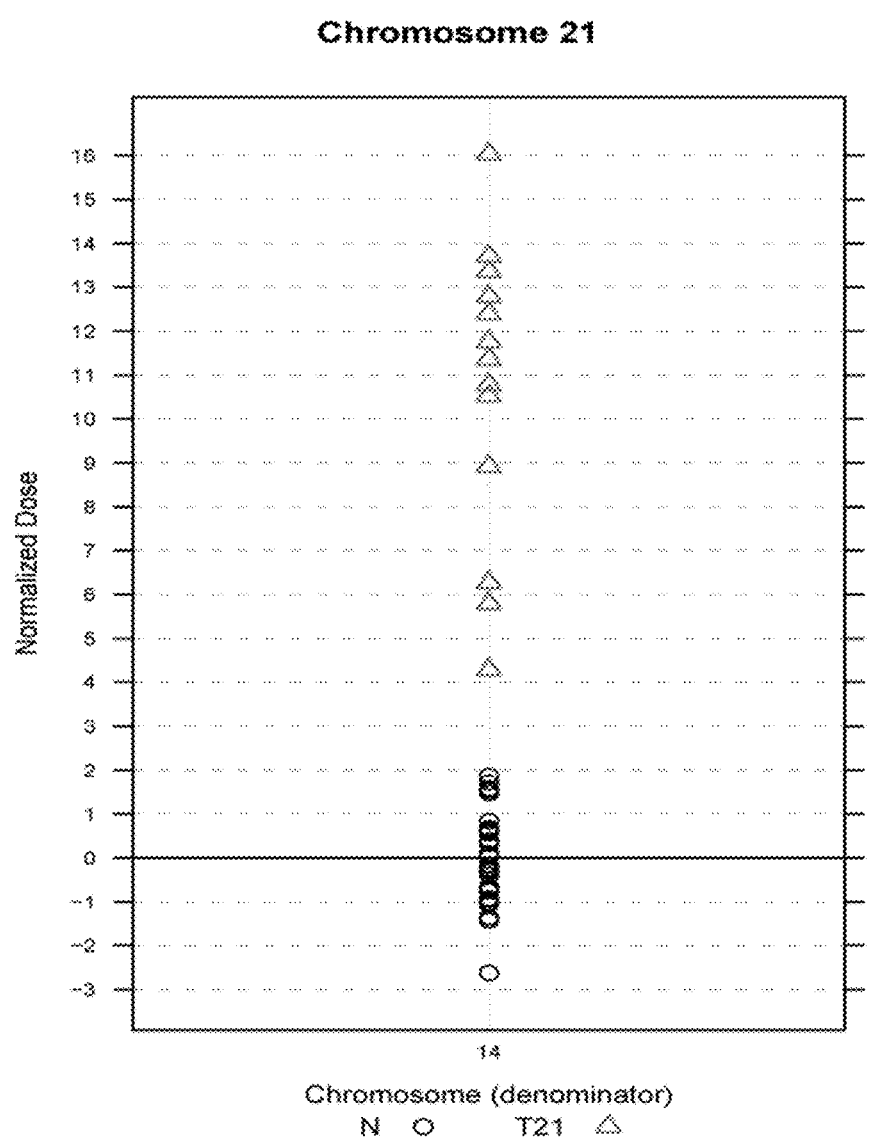
Figure 11:
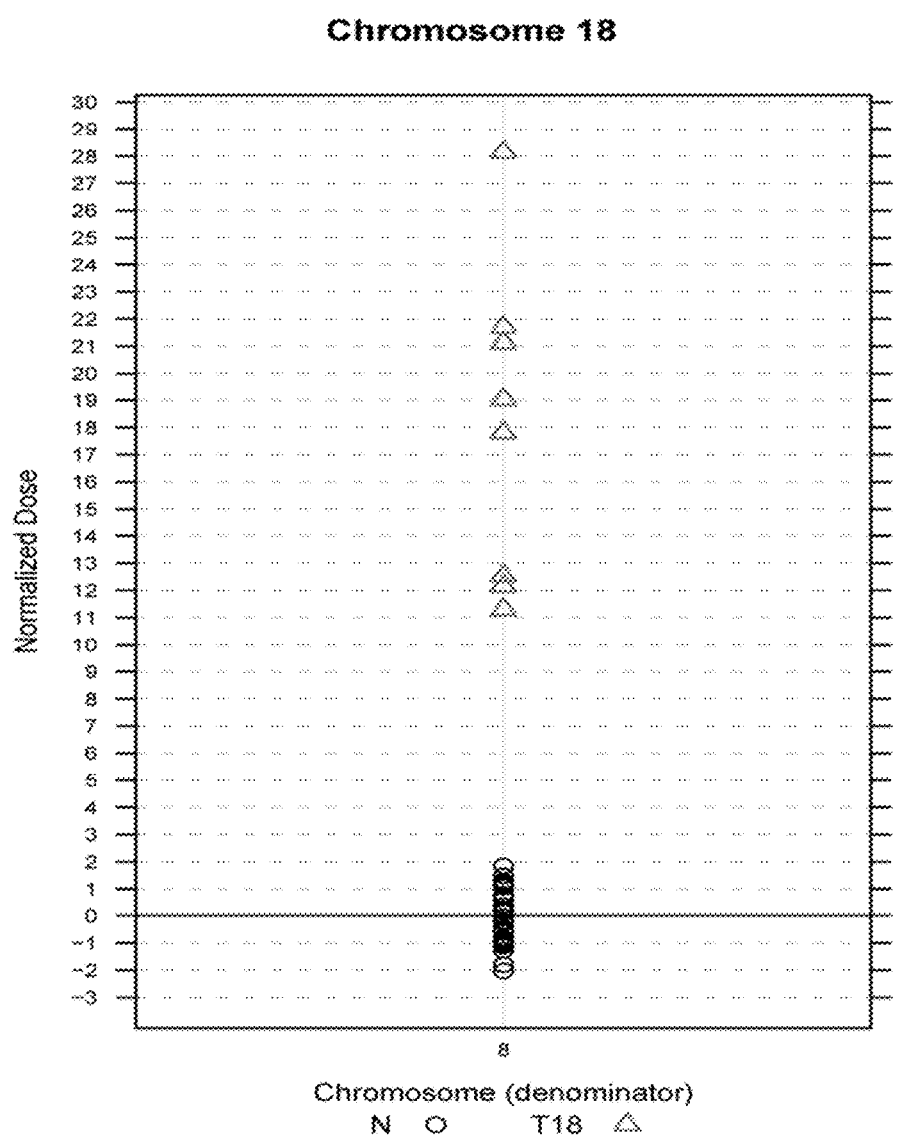
Figure 11:
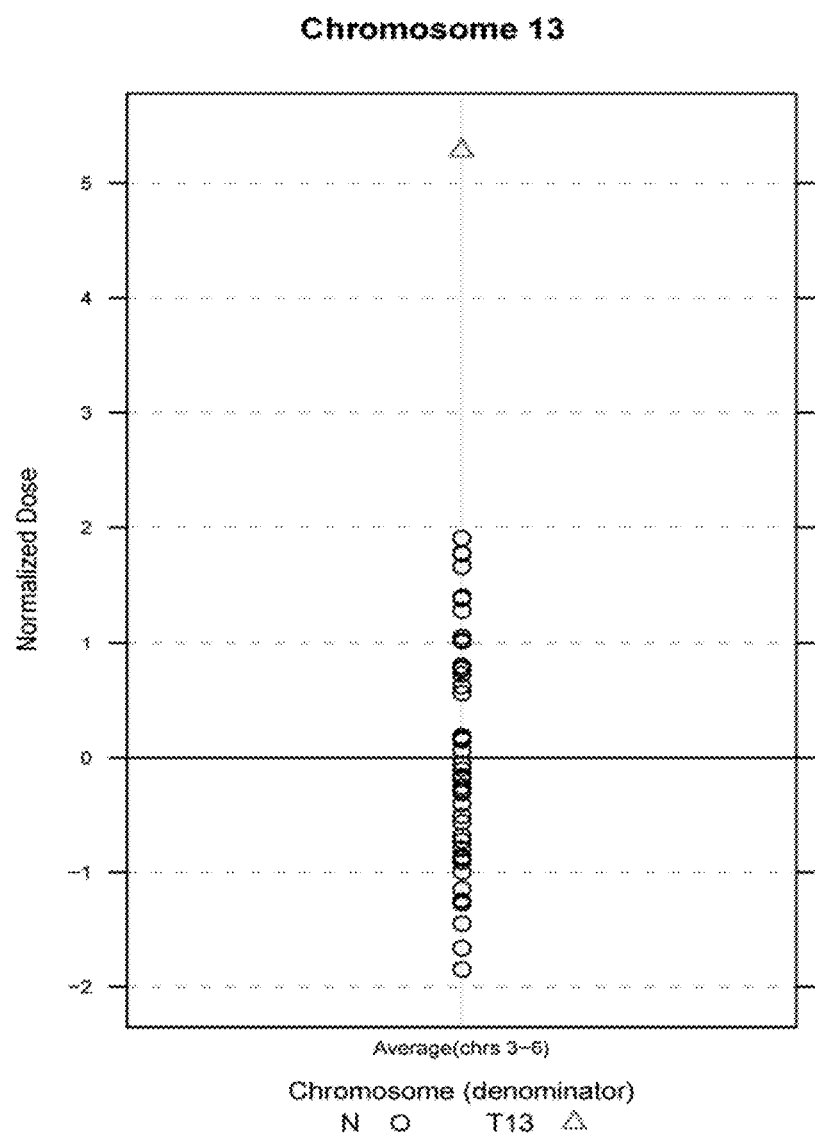
Figure 11D:
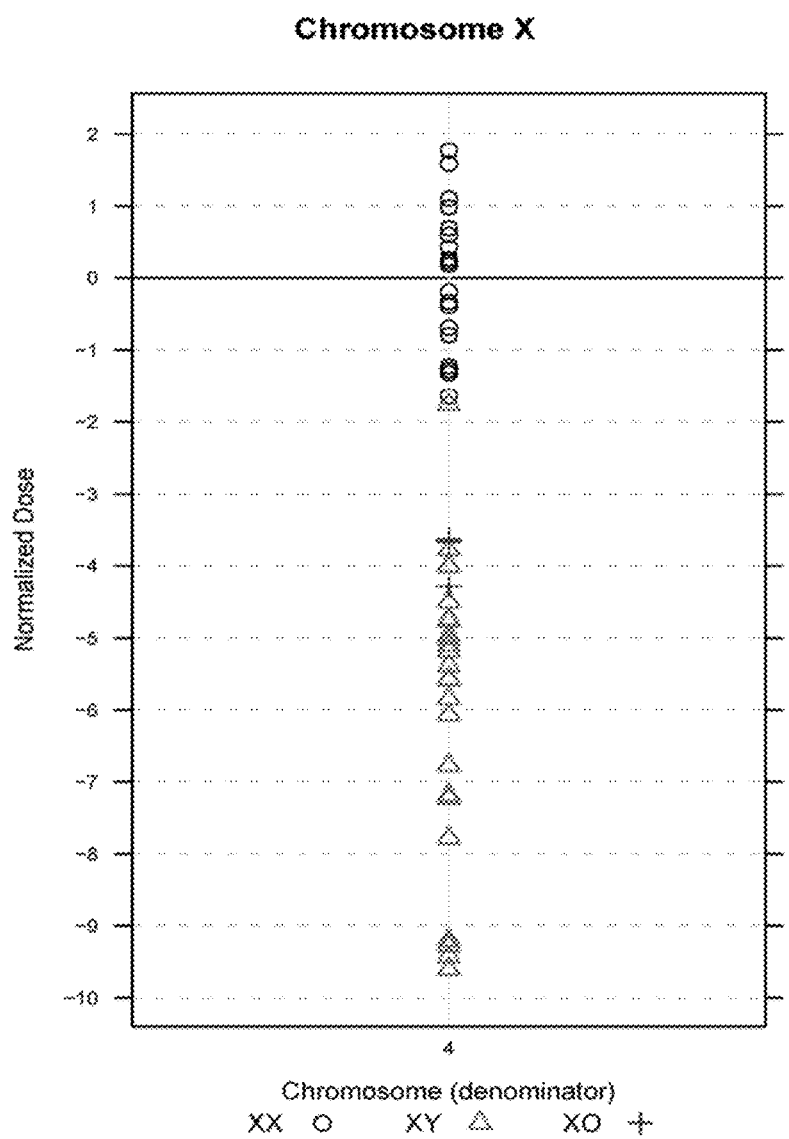
Figure 11:
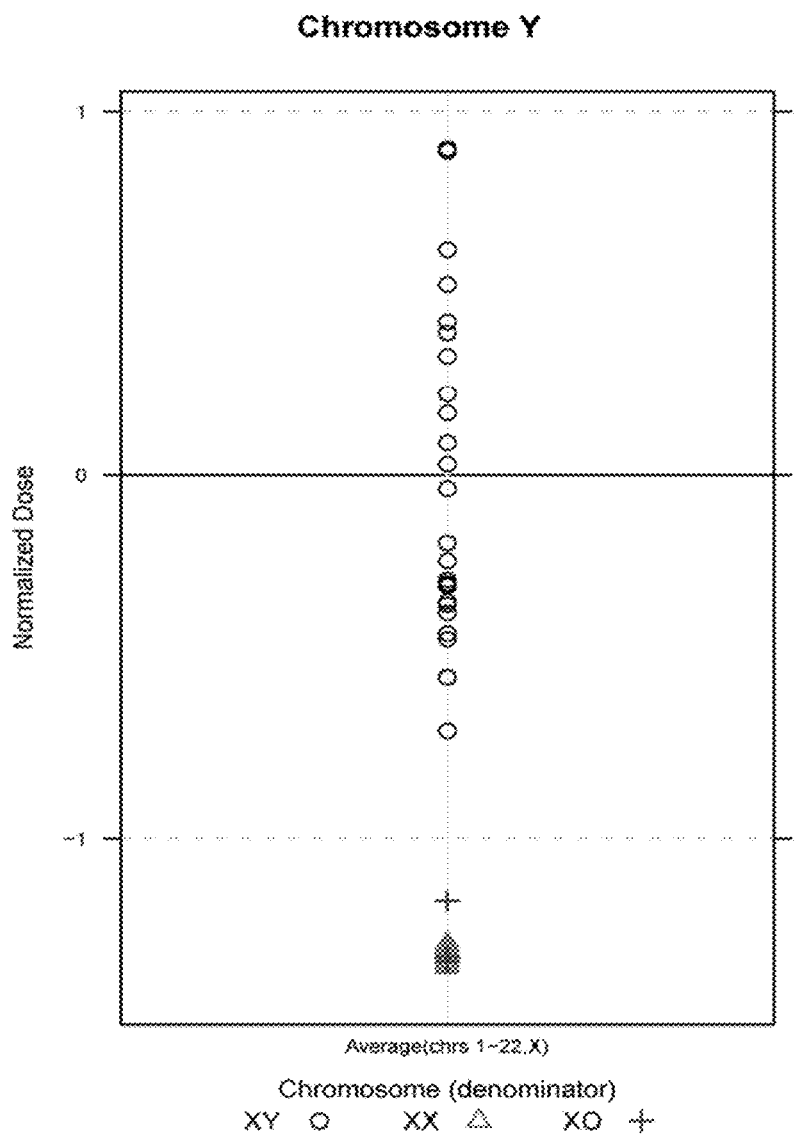

FIG. 11 (A) shows the distribution of chromosome doses relative to the standard deviation from the mean for chromosome 21 dose in the unaffected samples (o) and the trisomy 21 samples (T21; Δ) when using chromosome 14 as the normalizing chromosome for chromosome 21. FIG. 11 (B) shows the distribution of chromosome doses relative to the standard deviation from the mean for chromosome 18 dose in the unaffected samples (o) and the trisomy 18 samples (T18; Δ) when using chromosome 8 as the normalizing chromosome for chromosome 18. FIG. 11 (C) shows the distribution of chromosome doses relative to the standard deviation from the mean for chromosome 13 dose in the unaffected samples (o) and the trisomy 13 samples (T13; Δ), using the average sequence tag density of the group of chromosomes 3, 4, 5, and 6 as the normalizing chromosome to determine the chromosome dose for chromosome 13. FIG. 11 (D) shows the distribution of chromosome doses relative to the standard deviation from the mean for chromosome X dose in the unaffected female samples (o), the unaffected male samples (Δ), and the monosomy X samples (XO; +) when using chromosome 4 as the normalizing chromosome for chromosome X. FIG. 11 (E) shows the distribution of chromosome doses relative to the standard deviation from the mean for chromosome Y dose in the unaffected male samples (o the unaffected female sample s (Δ), and the monosomy X samples (+), when using the average sequence tag density of the group of chromosomes 1-22 and X as the normalizing chromosome to determine the chromosome dose for chromosome Y.

The data show that trisomy 21, trisomy 18, trisomy 13 were clearly distinguishable from the unaffected (normal) samples. The monosomy X samples were easily identifiable as having chromosome X dose that were clearly lower than those of unaffected female samples (FIG. 11 (D)), and as having chromosome Y doses that were clearly lower than that of the unaffected male samples (FIG. 11 (E)).

Therefore the method provided is sensitive and specific for determining the presence or absence of chromosomal aneuploidies in a maternal blood sample.

While preferred embodiments of the present invention have been shown and described herein, it will be obvious to those skilled in the an that such embodiments are provided by way of example only. Numerous variations, changes, and substitutions will now occur to those skilled in the an without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying fetal trisomy 21, said method comprising the steps:
    (a) sequencing at least a portion of fetal and maternal nucleic acids of a maternal blood sample to obtain sequence information and identifying at least $3\times10^6$ mapped sequence tags within the sequence information, wherein each mapped sequence tag maps uniquely to the human genome;
    (b) identifying and counting within the identified at least $3\times10^6$ mapped sequence tags the total number of each mapped sequence tag that maps to chromosome 21;
    (c) identifying and counting within the identified at least $3\times10^6$ mapped sequence tags the total number of each mapped sequence tag that maps to at least one normalizing chromosome;
    (d) using said total number of mapped sequence tags identified for chromosome 21 in step (b) and said total number of mapped sequence tags identified for said at least one normalizing chromosome in step (c) to calculate a chromosome dose for chromosome 21;
    wherein step (d) comprises:
        (i) calculating a sequence tag density ratio for chromosome 21, by normalizing said total number of mapped sequence tags identified for chromosome 21 in step (b) to the length of chromosome 21;
        (ii) calculating a sequence tag density ratio for said at least one normalizing chromosome, by normalizing said total number of mapped sequence tags identified for said at least one normalizing chromosome in step (c) to the length of said at least one normalizing chromosome; and
        (iii) using the sequence tag density ratios calculated in steps (i) and (ii) to calculate the chromosome dose for chromosome 21, wherein said chromosome dose is calculated as a ratio of said sequence tag density ratio for chromosome 21 and said sequence tag density ratio for said at least one normalizing chromosome; and
    (e) comparing said chromosome dose to at least one threshold value, and thereby identifying the presence or absence of fetal trisomy 21,
    wherein said normalizing chromosome is a chromosome or group of chromosomes that gives the smallest variability in chromosome dose across a plurality of qualified samples and/or gives the greatest differentiability in chromosome dose between an affected trisomy 21 sample from one or more unaffected samples.

2. The method of claim 1, wherein said fetal and maternal nucleic acid molecules are cell-free DNA molecules.

3. The method of claim 1, wherein said sequencing is performed on an amplified library preparation.

4. The method of claim 1, wherein said sequencing is next generation sequencing (NGS).

5. The method of claim 1, wherein said sequencing is massively parallel sequencing-by-synthesis with reversible dye terminators.

6. The method of claim 1, wherein said sequencing is sequencing-by-ligation.

7. The method of claim 1, wherein said sequencing is single molecule sequencing.

8. A method for identifying fetal trisomy 18, said method comprising the steps:
    (a) sequencing at least a portion of fetal and maternal nucleic acids of a maternal blood sample to obtain sequence information and identifying at least $3\times10^6$ mapped sequence tags within the sequence information, wherein each mapped sequence tag maps uniquely to the human genome;
    (b) identifying and counting within the identified at least $3\times10^6$ mapped sequence tags the total number of each mapped sequence tag that maps to chromosome 18;
    (c) identifying and counting within the identified at least $3\times10^6$ mapped sequence tags the total number of each mapped sequence tag that maps to at least one normalizing chromosome;
    (d) using said total number of mapped sequence tags identified for chromosome 18 in step (b) and said total number of mapped sequence tags identified for the at least one normalizing chromosome in step (c) to calculate a chromosome dose for chromosome 18;
    wherein step (d) comprises:
        (i) calculating a sequence tag density ratio for chromosome 18, by normalizing said total number of mapped sequence tags identified for chromosome 18 in step (b) to the length of chromosome 18;
        (ii) calculating a sequence tag density ratio for said at least one normalizing chromosome, by normalizing said total number of mapped sequence tags identified for said at least one normalizing chromosome in step (c) to the length of said at least one normalizing chromosome; and
        (iii) using the sequence tag density ratios calculated in steps (i) and (ii) to calculate the chromosome dose for chromosome 18, wherein said chromosome dose is calculated as a ratio of said sequence tag density ratio for chromosome 18 and said sequence tag density ratio for said at least one normalizing chromosome; and (e) comparing said chromosome dose to at least one threshold value, and thereby identifying the presence or absence of fetal trisomy 18, wherein said normalizing chromosome is a chromosome or group of chromosomes that gives the smallest variability in chromosome dose across a plurality of qualified samples and/or gives the greatest differentiability in chromosome dose between an affected trisomy 18 sample from one or more unaffected samples.

9. The method of claim 8, wherein said fetal and maternal nucleic acid molecules are cell-free DNA molecules.

10. The method of claim 8, wherein said sequencing is performed on an amplified library preparation.

11. The method of claim 8, wherein said sequencing is next generation sequencing (NGS).

12. The method of claim 8, wherein said sequencing is massively parallel sequencing-by-synthesis with reversible dye terminators.

13. The method of claim 8, wherein said sequencing is sequencing-by-ligation.

14. The method of claim 8, wherein said sequencing is single molecule sequencing.

15. A method for identifying fetal trisomy 13, said method comprising the steps:

(a) sequencing at least a portion of fetal and maternal nucleic acids of a maternal blood sample to obtain sequence information and identifying at least $3\times10^6$ mapped sequence tags within the sequence information, wherein each mapped sequence tag maps uniquely to the human genome;

(b) identifying and counting within the identified at least $3\times10^6$ mapped sequence tags the total number of each mapped sequence tag that maps to chromosome 13;

(c) identifying and counting within the identified at least $3\times10^6$ mapped sequence tags the total number of each mapped sequence tag that maps to at least one normalizing chromosome;

(d) using said total number of mapped sequence tags identified for chromosome 13 in step (b) and said total number of mapped sequence tags identified for the at least one normalizing chromosome in step (c) to calculate a chromosome dose for chromosome 13;

wherein step (d) comprises:

(i) calculating a sequence tag density ratio for chromosome 13, by normalizing said total number of mapped sequence tags identified for chromosome 13 in step (b) to the length of chromosome 13;

(ii) calculating a sequence tag density ratio for said at least one normalizing chromosome, by normalizing said total number of mapped sequence tags identified for said at least one normalizing chromosome in step (c) to the length of said at least one normalizing chromosome; and (iii) using the sequence tag density ratios calculated in steps (i) and (ii) to calculate the chromosome dose for chromosome 13, wherein said chromosome dose is calculated as a ratio of said sequence tag density ratio for chromosome 13 and said sequence tag density ratio for said at least one normalizing chromosome; and (e) comparing said chromosome dose to at least one threshold value, and thereby identifying the presence or absence of fetal trisomy 13, wherein said normalizing chromosome is a chromosome or group of chromosomes that gives the smallest variability in chromosome dose across a plurality of qualified samples and/or gives the greatest differentiability in chromosome dose between an affected trisomy 13 sample from one or more unaffected samples.

16. The method of claim 15, wherein said fetal and maternal nucleic acid molecules are cell-free DNA molecules.

17. The method of claim 15, wherein said sequencing is performed on an amplified library preparation.

18. The method of claim 15, wherein said sequencing is next generation sequencing (NGS).

19. The method of claim 15, wherein said sequencing is massively parallel sequencing-by-synthesis with reversible dye terminators.

20. The method of claim 15, wherein said sequencing is sequencing-by-ligation.

21. The method of claim 15, wherein said sequencing is single molecule sequencing.

* * * * *